(12) United States Patent
Grossman et al.

(10) Patent No.: US 10,758,175 B2
(45) Date of Patent: *Sep. 1, 2020

(54) METHODS AND APPARATUS FOR NEUROMODULATION

(71) Applicants: Massachusetts Institute of Technology, Cambridge, MA (US); NuVu LLC, Cambridge, MA (US)

(72) Inventors: Nir Grossman, Lorrach (DE); David Wang, Cambridge, MA (US); Edward Boyden, Chestnut Hill, MA (US)

(73) Assignees: Massachusetts Institute of Technology, Cambridge, MA (US); NuVu LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/571,845

(22) Filed: Sep. 16, 2019

(65) Prior Publication Data
US 2020/0008743 A1 Jan. 9, 2020

Related U.S. Application Data

(63) Continuation of application No. 15/215,597, filed on Jul. 21, 2016, now Pat. No. 10,448,883.
(Continued)

(51) Int. Cl.
*A61B 5/00* (2006.01)
*A61B 5/0476* (2006.01)
(Continued)

(52) U.S. Cl.
CPC ........ *A61B 5/4836* (2013.01); *A61B 5/04001* (2013.01); *A61B 5/0476* (2013.01);
(Continued)

(58) Field of Classification Search
USPC .............................................................. 601/2
See application file for complete search history.

(56) References Cited

U.S. PATENT DOCUMENTS

| 5,497,781 A | 3/1996 | Chen et al. |
| 6,901,353 B1 | 5/2005 | Huang |

(Continued)

OTHER PUBLICATIONS

Cen, L., et al., Real-time brain oscillation detection and phase-locked stimulation using autoregressive spectral estimation and time-series forward prediction; published in IEEE Trans Biomed Eng. Mar. 2013; 60(3); pp. 753-762.
(Continued)

*Primary Examiner* — Pierre E Elisca
(74) *Attorney, Agent, or Firm* — Stephen R. Otis

(57) ABSTRACT

A neuromodulator accurately measures—in real time and over a range of frequencies—the instantaneous phase and amplitude of a natural signal. For example, the natural signal may be an electrical signal produced by neural tissue, or a motion such as a muscle tremor. The neuromodulator generates signals that are precisely timed relative to the phase of the natural signal. For example, the neuromodulator may generate an exogenous signal that is phase-locked with the natural signal. Or, for example, the neuromodulator may generate an exogenous signal that comprises short bursts which occur only during a narrow phase range of each period of an oscillating natural signal. The neuromodulator corrects distortions due to Gibbs phenomenon. In some cases, the neuromodulator does so by applying a causal filter to a discrete Fourier transform in the frequency domain, prior to taking an inverse discrete Fourier transform.

20 Claims, 15 Drawing Sheets

Related U.S. Application Data

(60) Provisional application No. 62/194,942, filed on Jul. 21, 2015.

(51) Int. Cl.

| | | |
|---|---|---|
| *G06F 17/14* | (2006.01) | |
| *A61B 5/04* | (2006.01) | |
| *A61B 5/11* | (2006.01) | |
| *A61N 5/06* | (2006.01) | |
| *A61N 7/00* | (2006.01) | |

(52) U.S. Cl.
CPC .......... *A61B 5/1101* (2013.01); *A61B 5/7253* (2013.01); *A61B 5/7257* (2013.01); *A61N 5/0622* (2013.01); *A61N 7/00* (2013.01); *G06F 17/14* (2013.01); *A61N 2005/063* (2013.01); *A61N 2007/0021* (2013.01)

(56) References Cited

U.S. PATENT DOCUMENTS

| | | | |
|---|---|---|---|
| 7,024,447 | B2 | 4/2006 | Pisati et al. |
| 2006/0015034 | A1 | 1/2006 | Martinerie et al. |
| 2014/0142883 | A1 | 5/2014 | Bartley et al. |
| 2014/0336722 | A1 | 11/2014 | Rocon de Lima et al. |
| 2017/0323481 | A1* | 11/2017 | Tran .................. G06K 9/00771 |
| 2019/0060602 | A1* | 2/2019 | Tran .................. G06K 9/00671 |
| 2019/0125456 | A1* | 5/2019 | Shelton, IV ........... G16H 40/00 |
| 2019/0125457 | A1* | 5/2019 | Parihar .................. A61B 34/10 |
| 2019/0125459 | A1* | 5/2019 | Shelton, IV ..... A61B 17/07207 |

OTHER PUBLICATIONS

Feldman, M., Hilbert transform in vibration analysis; published in Mechanical Systems and Signal Processing, vol. 25, Issue 3, Apr. 2011, pp. 735-802.
Huang, D., Practical Implementation of Hilbert-Huang Transform algorithm, published in Acta Oceonologia Sinica, 22(1): 1-14, 2003.
Jensen, O., et al., Cross-frequency coupling between neuronal oscillations, published in Trends in Cognitive Sciences, vol. 11, Issue 7, Jul. 2007, pp. 267-269.
Niemitalo, O, O., Hilbert transform, published in iki.fi/o blog, last modified Aug. 28, 2014, accessed on Jul. 23, 2016 at http://yehar.com/blog/?p=368.
Pan, C., Gibbs phenomenon suppression and optimal windowing for attenuation and Q measurements; submitted to Geophysics SLAC-PUB-6222, Sep. 1993.
Pastor, J., et al., Hyper-Synchronization, De-Synchronization, Synchronization and Seizures, published as Chapter 6 of Epilepsy—Histological, Electroencephalographic and Psychological Aspects, edited by Dejan Stevanovic, 2012.
Riviere, C., et al., Adaptive canceling of physiological tremor for improved precision in microsurgery, published in IEEE Transactions on Biomedical Engineering, vol. 45, Issue 7, pp. 839-846, Jul. 1998.
Veluvolu, K., et al., Bandlimited Multiple Fourier Linear Combiner for Real-time Tremor Compensation; published in 2007 29th Annual International Conference of the IEEE Engineering in Medicine and Biology Society, pp. 2847-2850, Aug. 2007.
Wu, Z., et al., Ensemble Empirical Mode Decomposition: A Noise Assisted Data Analysis Method; published in Advances in Adaptive Data Analysis vol. 01, Issue 01, Jan. 2009.
Zhang, J., et al., Real-time modeling and prediction of physiological hand tremor; published in Proceedings, IEEE International Conference on Acoustics, Speech, and Signal Processing, 2005, vol. 5, pp. v/645-v/648, Mar. 2005.
Freeman, W., Hilbert transform for brain waves; published in Scholarpedia, 2(1):1338 (2007).
Lindsten, F., A remark on zero-padding for increased frequency resolution, published 2010, accessed Apr. 20, 2017 at https://www.control.isy.liu.se/student/tsrt78/zeropadding.pdf.
Gold, et. al, Theory and Implementation of the Discrete Hilbert Transform; presented at Symposium on Computer Processing in Communications, Apr. 1969, accessed Apr. 20, 2017 at http://www.rle.mit.edu/dspg/documents/HilbertComplete.pdf.
Marple, S., Computing the discrete-time 'analytic' signal via FFT; published in Conference Record of the Thirty-First Asilomar Conference on Signals, Systems & Computers, 1997.
Brookes, M., "5: Gibbs Phenomenon", published 2014, accessed Apr. 20, 2017 at http://www.ee.ic.ac.uk/hp/staff/dmb/courses/E1Fourier/00500_GibbsPhenomenon_p.pdf.
Cagnan, H., et al., Phase dependent modulation of tremor amplitude in essential tremor through thalamic stimulation; published in Brain, vol. 136, No. 10, pp. 3062-3075 (Sep. 2013).

* cited by examiner

METHODS AND APPARATUS FOR NEUROMODULATION

RELATED APPLICATIONS

This application is a continuation of U.S. application Ser. No. 15/215,597 filed on Jul. 21, 2016, which claims the benefit of U.S. Provisional Application No. 62/194,942, filed Jul. 21, 2015 (the "Provisional"). The entire disclosure of the Provisional is herein incorporated by reference.

STATEMENT REGARDING FEDERALLY SPONSORED RESEARCH OR DEVELOPMENT

This invention was made with government support under Grant No. DP1 NS087724 awarded by the National Institutes of Health. The government of the United States of America has certain rights in the invention.

FIELD OF TECHNOLOGY

The present invention relates generally to neuromodulation and correcting distortion due to Gibbs phenomenon.

COMPUTER PROGRAM LISTING

Attached are twelve ASCII text files (collectively, the "Source Code"): (1) ECHT_ino.txt, created Jul. 12, 2016 with a size of about 17 KB; (2) FFT_C.txt, created Jul. 16, 2016 with a size of about 5 KB; (3) FFT_H.txt, created Jul. 16, 2016 with a size of about 1 KB; (4) ButterworthBandpass_h.txt, created Jul. 16, 2016 with a size of about 3 KB; (5) liir_c.txt, created Jul. 16, 2016 with a size of about 16 KB; (6) iir_h.txt, created Jul. 16, 2016 with a size of about 1 KB; (7) VarSizeSplitRadixRealP_cpp.txt, created Jul. 16, 2016 with a size of about 8 KB; (8) VarSizeSplitRadixRealP_h.txt, created Jul. 16, 2016 with a size of about 1 KB; (9) VarSizeRadix4_cpp.txt, created Jul. 16, 2016 with a size of about 8 KB; (10) VarSizeRadix4_h.txt, created Jul. 16, 2016 with a size of about 2 KB; (11) waveconst_h.txt, created Jul. 16, 2016 with a size of about 34 KB; and (12) window_h.txt, created Jul. 16, 2016 with a size of about 3 KB. The Source Code comprises a computer program listing for software in a prototype implementation of this invention. The Source Code is incorporated by reference herein.

SUMMARY

In illustrative implementations of this invention, a neuromodulator accurately measures—in real time and over a range of frequencies—the instantaneous phase and amplitude of a natural signal. For example, the natural signal may be (a) an electrical signal produced by neural tissue, or (b) a motion such as a muscle tremor.

This ability to take accurate, real-time measurements of instantaneous phase and amplitude of a natural signal is highly advantageous. It enables the neuromodulator to generate signals ("exogenous signals") that are precisely timed relative to the phase of the natural signal. For example, the neuromodulator may generate an exogenous signal that is phase-locked with the natural signal. Or, for example, the neuromodulator may generate an exogenous signal that comprises short bursts which occur only during a narrow phase range of each period of an oscillating natural signal.

In illustrative implementations of this invention, the neuromodulator (a) detects the instantaneous phase and amplitude of the natural signal in real time and (b) based on that instantaneous phase and amplitude, precisely controls timing of the exogenous signal relative to the phase of the natural signal, in order to achieve a desired therapeutic effect. Here are three non-limiting examples (A, B, and C):

Example A: In some implementations of this invention, a neuromodulator treats pathologic hyper-synchronization of brain tissue, such as the hyper-synchronization that occurs in tremors and epileptic seizures. The neuromodulator does so by generating an exogenous signal that is precisely timed relative to the phase of the natural signal. For instance, the neuromodulator may generate an exogenous signal which is anti-phasic relative to a natural neural signal (i.e., which is 180 degrees in phase apart from the endogenous signal). Or, for instance, the neuromodulator may generate an exogenous signal with a phase such that the exogenous signal tends to excite the neural tissue during refractory portions of periodic neural activity, and thus tends to inhibit the recharging of the neural tissue during the refractory portions, and thus tends the reduce the excitability of the neural tissue in subsequent (excitable) portions of the periodic neural activity. In either case in this Example A, an effect of the exogenous signal may be to reduce the amplitude of a brain signal and to otherwise cause neural activity to no longer be hyper-synchronized.

Example B: In some implementations of this invention, a neuromodulator enhances a target pattern of physiological activity. Again, the neuromodulator does so by generating an exogenous signal that has a precisely controlled phase. For instance, the neuromodulator may generate an exogenous signal that has the identical phase as a physiological signal. Or, for instance, the neuromodulator may generate an exogenous signal with a phase such that the exogenous signal tends to stimulate the neural tissue during peak (excitable) portions of a periodic physiological signal, and thus tends to make the neural tissue more excitable. In either case in this Example B, an effect of the exogenous signal may be to (a) increase the amplitude of a physiological signal or (b) cause the physiological signal to "entrain" with the exogenous signal (i.e., cause the phase of the physiological signal to be reset to match that of the exogenous signal).

Example C: In some implementations of this invention, a neuromodulator enhances a low frequency pattern of neural activity by generating short bursts of a higher frequency exogenous signal. While doing so, the neuromodulator precisely controls timing of the exogenous signal relative to the phase of the neural signal. For instance, the neuromodulator may generate the short bursts of the higher frequency exogenous signal, such that the short bursts occur only at a particular phase (or range of phases) during each period of a lower frequency neural signal. For instance, in some cases: (a) the low frequency neural signal is in the theta range (4-8 Hz), (b) the higher frequency exogenous signal is in the gamma range (30-70 Hz), (c) the short bursts of the higher frequency signal occur only at a specific phase (e.g., a phase or trough) of the lower frequency neural signal, (d) only one short burst of the high frequency signal is applied in each period of the lower frequency neural signal, and (e) each short burst of the high frequency signal comprises multiple periods of the higher frequency signal.

In order to understand why the present invention is able to take accurate real-time measurements of instantaneous phase and amplitude of a sensor signal, it is helpful to consider challenges involved in computing these instantaneous attributes.

The estimation of instantaneous attributes of a real-valued periodic signal (e.g., amplitude, phase and frequency) is done most efficiently with a version of the signal, known as the analytic signal. The analytic signal is complex (in the sense of complex numbers with real and imaginary parts). The real part of the analytic signal is the given real-valued signal and the imaginary part of the analytic signal is its Hilbert transform.

A popular, conventional strategy for computing the analytic signal and the Hilbert transform signal is: (a) to compute a discrete Fourier transform (DFT) of the real-valued signal and thus to represent the signal in the frequency domain; (b) to manipulate the frequency domain representation to remove the negative frequencies; and then (c) to construct the complex analytic signal using the inverse discrete Fourier transform (IDFT).

This popular strategy suffers from distortion, known as the Gibbs phenomenon, at the ends of the sample data resulting in erroneous estimations of the most recent attributes. Specifically, the Gibbs phenomenon distortion in the analytic signal stems from the properties of the DFT-IDFT process that converts the sampled time domain data into its frequency domain representation and then reconstructs a time domain signal. As long as the signal satisfies the Dirichlet conditions (most practical signals), the DFT-IDFT recovers any point of the original signal apart from points of "jump-discontinuity", where the Fourier series converges to the midpoint (average value of the discontinuity). The DFT produces a frequency domain representation of a discrete, finite time signal as if the signal were repeated periodically. Thus, if the last and first time-points of the signal do not have the same phase and are not continuously differentiable, the DFT encounters a jump-discontinuity between the signal ends In the frequency domain, the jump-discontinuity is represented with a spreading out of the spectrum over many frequencies. The result is an analytic signal and a Hilbert transform signal with erroneous amplitude and phase near the last and first sample points.

In illustrative implementations of this invention, the neuromodulator corrects distortion due to the Gibbs phenomenon by performing an algorithm that we loosely call Endpoint-corrected Hilbert transform (ECHT).

In some cases, the neuromodulator corrects the Gibbs phenomenon by performing what we call "frequency domain" ECHT or by performing what we call "front-padded time domain" ECHT. Both of these approaches may correct the Gibbs phenomenon by ensuring that a signal will be continuous and differentiable at the original end of the signal when a replica of the signal is appended to the signal, as occurs in the DFT of a finite signal. In "frequency domain" ECHT, the neuromodulator performs a DFT to calculate a frequency domain representation of a signal. The neuromodulator then applies a causal filter to the frequency domain representation, prior to an IDFT step. In "front-padded time domain" ECHT, the neuromodulator front-pads the signal with a copy of an end segment of the signal, then applies a causal filter to the padded signal, and then removes the added segment in the time domain, prior to the DFT and IDFT steps. In both of these approaches, the correction is made before the IDFT step that results in an analytic signal. The neuromodulator selectively deforms the beginning of the signal either in the frequency domain (in "frequency domain" ECHT) or in the time domain (in "front-padded time domain" ECHT) and does not deform the end of the signal. In both "frequency domain" ECHT and "front-padded time domain" ECHT, the value of the end of the signal is not changed, but the value of the beginning of the signal is changed, such that the value of the signal at the beginning and end of the signal is the same. Thus, in some cases, if a replica of the signal is appended to the signal at the original end of the signal (as is done during the DFT of a finite signal), the appended signal is continuously differentiable at the original end of the signal. By removing the jump discontinuity at that point, the neuromodulator eliminates (or significantly reduces) the Gibbs phenomenon distortions at the end of the analytic signal that results from taking an IDFT. This allows a computer to accurately calculate instantaneous phase and instantaneous amplitude at the end of the analytic signal (which corresponds in time to the end of the original signal).

In some cases, the neuromodulator corrects the Gibbs phenomenon by performing what we call "end-padded time domain" ECHT. In this approach, in some cases, the neuromodulator appends a segment of data values (e.g., zeros) of at least one period length to the end of the signal and then applies a causal filter, which has the directionality property, to make the padded signal continuous and differentiable at the endpoint of the original signal without deforming the original end of the signal. By pushing away the end of the padded signal from the original end before the DFT procedure, the neuromodulator ensures that the Gibbs distortion occurs away from the original end of the signal. Again, this allows a computer to accurately calculate instantaneous phase and instantaneous amplitude at t_now (the point in the analytic signal that corresponds in time to the end of the original signal).

ECHT maintains the same complexity class as the Hilbert transform, with worse case running time of $O(n \log(n))$ for n samples. Thus, ECHT is suitable for real-time computation of instantaneous attributes in simple hardware.

The description of the present invention in the Summary and Abstract sections hereof is just a summary. It is intended only to give a general introduction to some illustrative implementations of this invention. It does not describe all of the details and variations of this invention. Likewise, the description of this invention in the Field of Technology section is not limiting; instead it identifies, in a general, non-exclusive manner, a technology to which exemplary implementations of this invention generally relate. Likewise, the Title of this document does not limit the invention in any way; instead the Title is merely a general, non-exclusive way of referring to this invention. This invention may be implemented in many other ways.

BRIEF DESCRIPTION OF THE DRAWINGS

FIG. 10A shows a discrete signal that is a sampling of a natural signal; (b) FIG. 10B and FIG. 10C show the amplitude and phase, respectively, of the Fourier transform of the discrete signal; (c) FIG. 10D and FIG. 10E show the amplitude and phase, respectively, of the Fourier transform of the analytic signal; (d) FIG. 10F shows the correct and the computed Hilbert transform signal; (e) FIG. 10G shows the correct and the computed instantaneous amplitude A[n] values near the sample endpoint; and (f) FIG. 10H shows the correct and the computed instantaneous phase φ[n] values near the sample endpoint.

FIG. 11A shows a zero-padded signal before and after it is smoothed by a causal filter in the time domain; (b) FIG. 11B and FIG. 11C show the amplitude and phase, respectively, of the Fourier transform of the smoothed, padded signal; (c) FIG. 11D and FIG. 11E show the amplitude and phase, respectively, of the Fourier transform of the analytic signal; (d) FIG. 11F shows the correct and the computed Hilbert transform signal; (e) FIG. 11G shows the correct and the computed instantaneous amplitude A[n] values near the sample endpoint; and (f) FIG. 11H shows the correct and the computed instantaneous phase φ[n] values near the sample endpoint.

FIG. 12A and FIG. 12B show the amplitude and phase, respectively, of the Fourier transform of the analytic signal; (b) FIG. 12C shows the correct and the computed Hilbert transform signal; (e) FIG. 12D shows the correct and the computed instantaneous amplitude A[n] values near the sample endpoint; and (f) FIG. 12E shows the correct and the computed instantaneous phase φ[n] values near the sample endpoint.

The above Figures show some illustrative implementations of this invention, or provide information that relates to those implementations. However, this invention may be implemented in many other ways.

DETAILED DESCRIPTION

Neuromodulator

Figure 1:
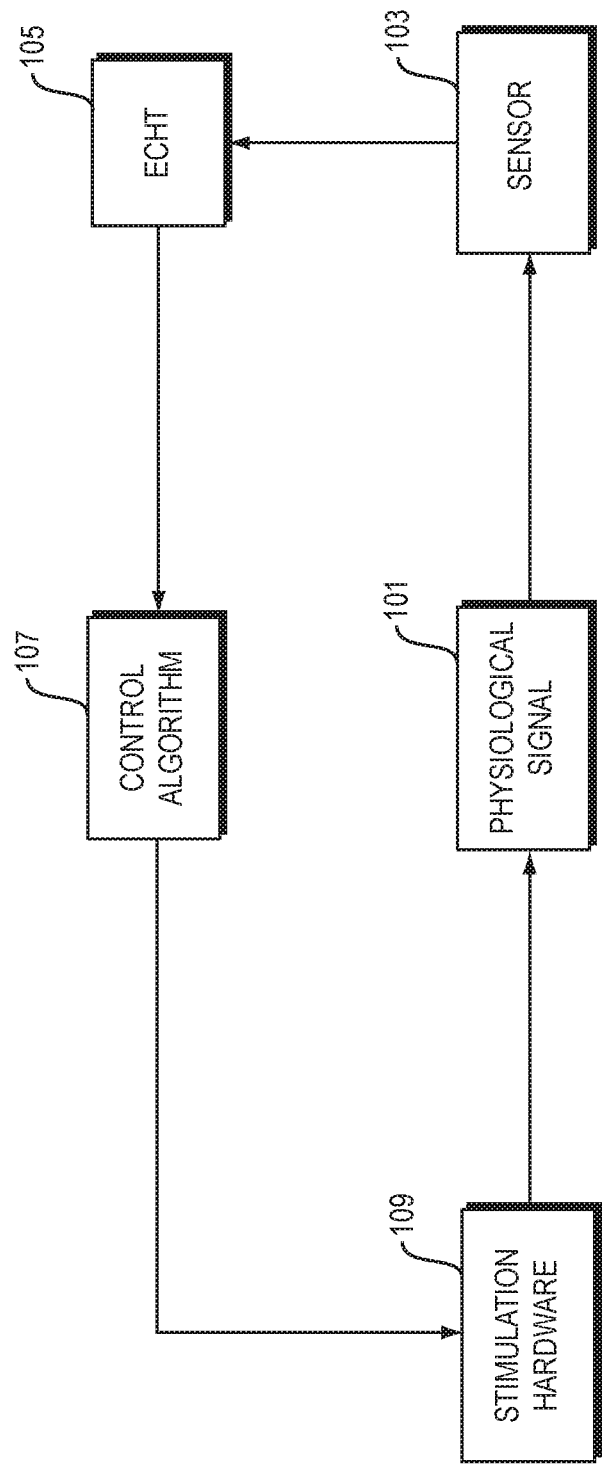
FIG. 1 is a flowchart of steps in a method of neuromodulation.

FIG. 1 is a flowchart of steps in a method of neuromodulation, in an illustrative implementation of this invention. In the example shown in FIG. 1, the method includes the following steps: A physiological signal (such as neural activity, or a muscle tremor that is caused by pathological neural activity) occurs in a patient (Step 101). A sensor takes sensor readings of the physiological activity (Step 103). A computer performs what we call an Endpoint-Corrected Hilbert Transform (ECHT) calculation. In this ECHT calculation, the computer determines in real time, based on the sensor readings, the instantaneous phase and instantaneous amplitude of the physiological signal (Step 105). A computer performs a control algorithm. In this algorithm, the computer takes the instantaneous phase and amplitude as an input, and outputs signals to control stimulation hardware (Step 107). The stimulation hardware outputs a neuromodulation signal. For example, the neuromodulation signal may comprise an electrical signal, magnetic signal, light signal, ultrasound signal or haptic signal. The neuromodulation signal directly or indirectly affects neural activity of the patient, and thus modifies the physiological signal (Step 109).

Figure 2:
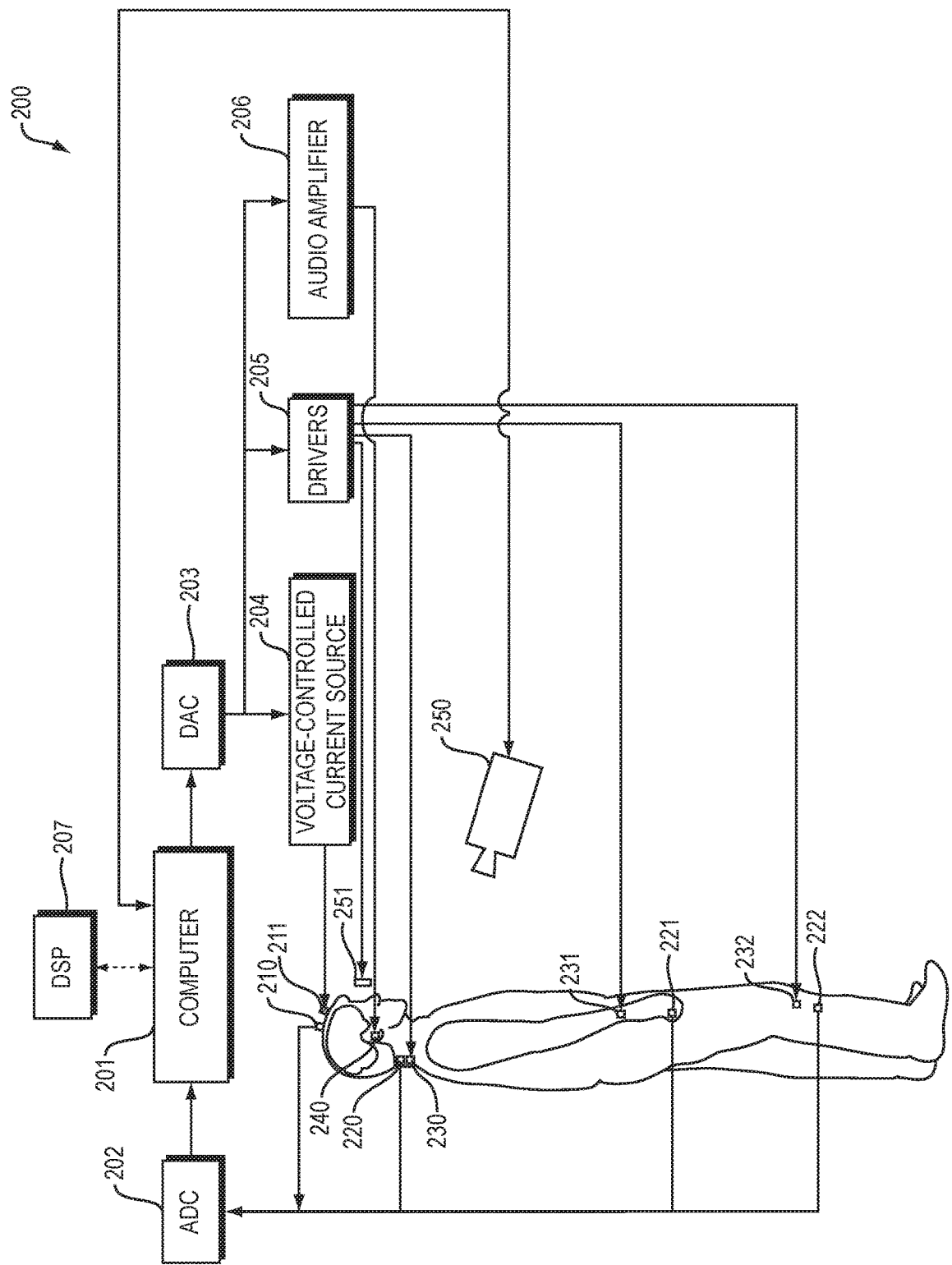
FIG. 2 is a diagram of hardware for neuromodulation.

FIG. 2 is a diagram of a neuromodulator, in an illustrative implementation of this invention. In the example shown in FIG. 2, the neuromodulator includes sensors 210, 220, 221, 222, an ADC (analog-to-digital converter) 202, a computer 201, a DSP (digital signal processor) 207, a DAC (digital-to-analog converter) 203, a VCCS (voltage controlled current source) 204, drivers 205, and an audio amplifier 206. The DSP is optional. In some cases, computations are performed by a microcontroller, without using a DSP.

In the neuromodulator shown in FIG. 2, sensors record one or more physiological signals. For example: (a) one of more external electrodes 210 may take EEG (electroencephalography) measurements of neural activity; (b) motion sensors 220, 221, 222 may take measurements of motion, such as measurements of a muscle tremor caused by pathologic neural activity (e.g., due to Parkinson's disease); and (c) one or more cameras (e.g., 250) may capture video images of motion, such as a tremor. For example, each of the motion sensors 220, 221, 222 may comprise a three-axis digital gyroscope and three-axis digital accelerometer. In some cases, sensors (such as EEG sensor 210 and motion sensors 220, 221, 222) may output analog signals that encode measurements taken by the sensors. In some cases, sensors (such as camera 250) may output digital signals that encode sensor measurements. For the sensors that output analog signals, an ADC (analog-to-digital converter) 202 may convert these analog signals into digital signals.

In the neuromodulator shown in FIG. 2, a computer 201 takes sensor readings as an input, in digital form. The computer 201 performs an ECHT algorithm to determine the instantaneous phase and amplitude of one or more physiological signals (e.g., neural activity or a tremor indicative of neural activity). The computer 201 may also interface with a DSP (digital signal processor) 207 that processes incoming and outgoing digital signals. The computer outputs digital signals. A DAC (digital-to-analog converter) 203 converts these digital signals to analog signals.

In the neuromodulator shown in FIG. 2, an analog voltage signal produced by a DAC 203 may control a VCCS (voltage-controlled current source) 204, which in turn may output an electrical current that is delivered to a patient via one or more electrodes. For example, external electrode 211 may deliver transcranial electrical stimulation to the brain of the patient. Electrodes for delivering electrical stimulation may be placed in any position on the head or skin of the patient or may be implanted inside a patient. The electrical current that is delivered to the patient via these one or more electrodes may comprise an electrical neuromodulation signal.

In some cases, the VCCS includes one or more OTAs (operational transconductance amplifiers) or operational amplifiers. In some cases, the VCCS may be a component of a bi-phasic current source, such as a Digitimer® DS4 Bi-phasic Stimulus Isolator.

In the neuromodulator shown in FIG. 2, one or more analog signals from a DAC 203 may control one or more drivers 205. The drivers 205 may in turn control one or more transducers that output a signal that affects neural activity in the patient. For example, the transducers may include one or more light sources 251 that display visual neuromodulation signals to a patient. For instance, the light sources 251 may comprise (i) a computer screen, virtual reality screen, augmented reality display, or other electronic display screen, or (ii) an array of LEDs (light-emitting diodes). In some cases, the transducers may include one or more haptic transducers 230, 231, 232 for delivering tactile/haptic neuromodulation signals to a patient.

In the neuromodulator shown in FIG. 2, one or more analog signals from a DAC 203 may control one or more audio amplifiers 206. The amplifiers 206 may in turn control one or more audio transducers (e.g., 240). For example, the audio transducers may include one or more headphones, earbuds, earphones or speakers that deliver audible neuromodulation signals.

Figure 3B:
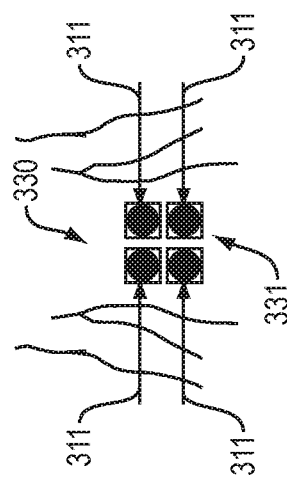
FIG. 3B shows an implantable electrode and an external recording electrode.
Figure 3D:
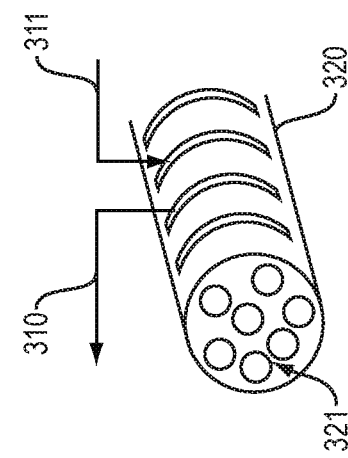
FIG. 3D shows external electrodes for transcutaneous stimulation.
Figure 3A:
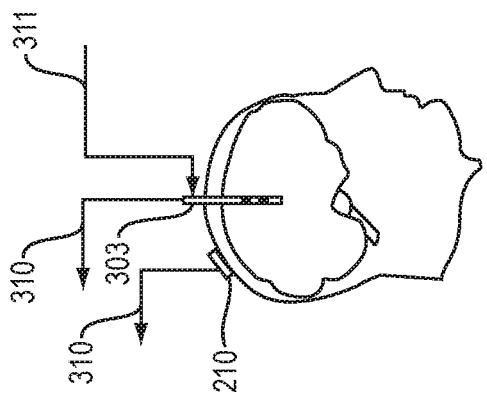
FIG. 3A shows an electrode that delivers a therapeutic electrical signal and detects electrical activity produced by tissue.

FIG. 3A shows an electrode 301 that both delivers a therapeutic electrical signal to neural tissue and detects electrical activity produced by neural tissue, in an illustrative implementation of this invention. For example, the operation of electrode 301 may time-multiplexed, such that electrode 301 takes sensor readings at different times than when it delivers electrical stimulation.

In FIGS. 3A, 3B, 3C, 3D, 4A, 4B and 5: (a) each arrow 310 signifies that sensor readings are being output by a sensor; and (b) each arrow 311 signifies that a signal (e.g., an electrical signal from DAC 203, VCCS 204, drivers 205 or audio amplifier 206) is being delivered to stimulation hardware.

FIG. 3B shows an implantable electrode 303 and an external recording electrode 210, in an illustrative implementation of this invention. For example, the implantable electrode 303 may stimulate brain tissue (cortex or deeper), or record neural activity, or both. The implantable electrode 303 may be used alone or together with external recording electrode 210. For example, the recording electrode 210 may record neural activity that has been affected by stimulation from implantable electrode 303.

Figure 3C:
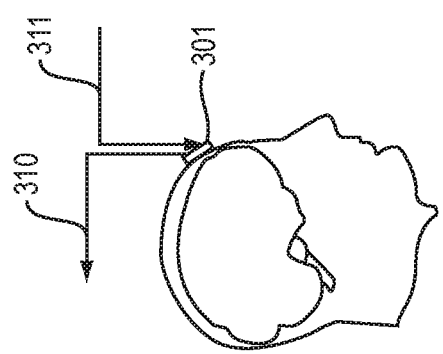
FIG. 3C shows a cuff electrode.

FIG. 3C shows a cuff electrode 320 for recording neural activity (e.g., of nerve 321), in an illustrative implementation of this invention.

FIG. 3D shows four external electrodes 331 for transcutaneous stimulation, in an illustrative implementation of this invention. In the example shown in FIG. 3D, the electrodes 331 are positioned on the skin of the back 330 of a patient.

Figure 4B:
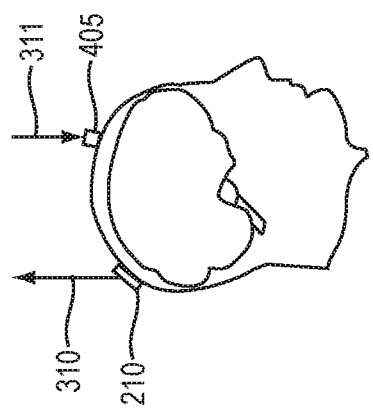
FIG. 4B shows an ultrasound transducer and an external recording electrode.
Figure 4A:
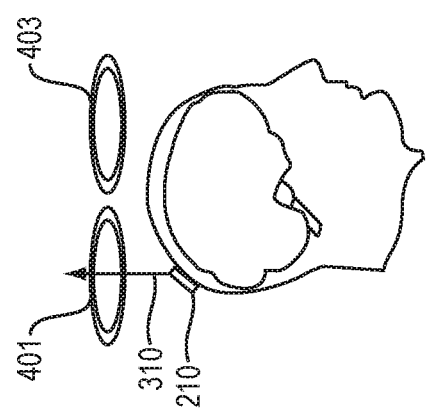
FIG. 4A shows magnetic coils for magnetic stimulation and an external recording electrode.

FIG. 4A shows magnetic coils 401, 403 for magnetic stimulation and an external recording electrode 210, in an illustrative implementation of this invention. In the example shown in FIG. 4A, magnetic coils 401, 403 deliver magnetic stimulation to the brain of a patient.

FIG. 4B shows an ultrasound transducer 405 and an external recording electrode 210, in an illustrative implementation of this invention. In the example shown in FIG. 4B, ultrasound transducer 405 delivers ultrasound stimulation to the brain of a patient.

Figure 5:
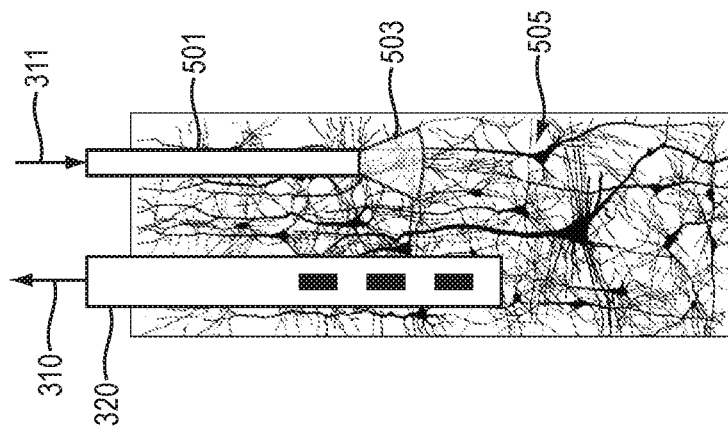
FIG. 5 shows an implantable optic fiber for optogenetic stimulation and an implantable recording electrode.

FIG. 5 shows an implantable optic fiber 501 for optogenetic stimulation and an implantable recording electrode 320, in an illustrative implementation of this invention. The optic fiber 501 delivers light stimulation 503 to transfected neural tissue (e.g., 505). The transfected neural tissue has been optogenetically modified such that exposing the transfected neural tissue to certain wavelengths of light triggers a response in the tissue, such as stimulation or suppression of activity of the tissue. The recording electrode 320 may record neural activity that has been affected by light stimulation from optic fiber 401.

Endpoint-Corrected Hilbert Transform, Generally

In illustrative implementations of this invention, one or more computers (e.g., in a neuromodulator) perform what we call "Endpoint Corrected Hilbert Transform" or "ECHT". The ECHT algorithm corrects distortion due to Gibbs phenomenon that occurs when calculating instantaneous attributes (e.g. instantaneous phase and amplitude) of a signal using an FFT/IFFT procedure.

Advantageously, ECHT is computationally efficient. This computational efficiency allows ECHT to compute instantaneous phase and amplitude in real time using inexpensive, off-the-shelf, computer processors.

The runtime complexity of the conventional Hilbert transform (without correction for the Gibbs phenomenon) for n samples is O(n log(n)), which is dominated by the FFT-IFFT operations. Both the FFT (fast Fourier transform) and the IFFT (inverse fast Fourier transform) have a complexity of O(n log(n)). Amelioration of the Gibbs phenomenon using recursive models, such as autoregression or polynomial fitting, may add a parameters estimation operation (e.g. Yule-Walker method) with a runtime complexity of $O(n^3)$ and known theoretical limit of $O(n^{2.81})$. In comparison, in illustrative implementations of this invention, ECHT adds a simple filtering operation with a runtime complexity of O(n), thus maintaining an overall O(n log(n)) complexity of the Hilbert transform.

In illustrative implementations of this invention, one or more computer processors perform an ECHT algorithm, thereby achieving zero-phase-lag real-time computation of the Hilbert transform with minimal computing power. This in turn allows sophisticated tracking and closed-loop applications in affordable and portable hardware.

The following is a description of three types of ECHT: specifically, what we call (1) "frequency domain" ECHT; (2) "end-padded time domain" ECHT, and (3) "front-padded time domain" ECHT.

"Frequency Domain" ECHT

In some implementations of this invention, one or more computers (e.g., in a neuromodulator) perform what we call "frequency domain" ECHT. In these cases, causal smoothing occurs in the frequency domain.

In some cases, "frequency domain" ECHT corrects the Gibbs phenomenon by ensuring that a signal will be continuous and differentiable at the original end of the signal when a replica of the signal is appended to the signal, as occurs in the DFT of a finite signal. In "frequency domain" ECHT, a computer applies a causal filter to the frequency domain representation of a signal. This filter is applied after the DFT that results in the frequency domain representation of the signal, but before the IDFT step that results in an analytic signal. The causal filtering preserves the values at the end of the signal while selectively deforming the values at the beginning of the signal. Thus, in some cases, if a replica of the signal is appended to the signal at the original end of the signal (as is done during the DFT of a finite signal), the appended replica is continuously differentiable at the original end of the signal. By removing the jump discontinuity at that point, a computer eliminates (or significantly reduces) the Gibbs phenomenon distortions at the end of the analytic signal that results from taking an IDFT. This allows a computer to accurately compute instantaneous phase and instantaneous amplitude at the end of the analytic signal (which corresponds in time to the end of the original signal). In "frequency domain" ECHT, the start and end values of the causally smoothed signal in the frequency domain are the same, and thus, after the IDFT, the start and end values of the Hilbert transform (which is the imaginary component of the analytic signal) are the same.

Figure 6:
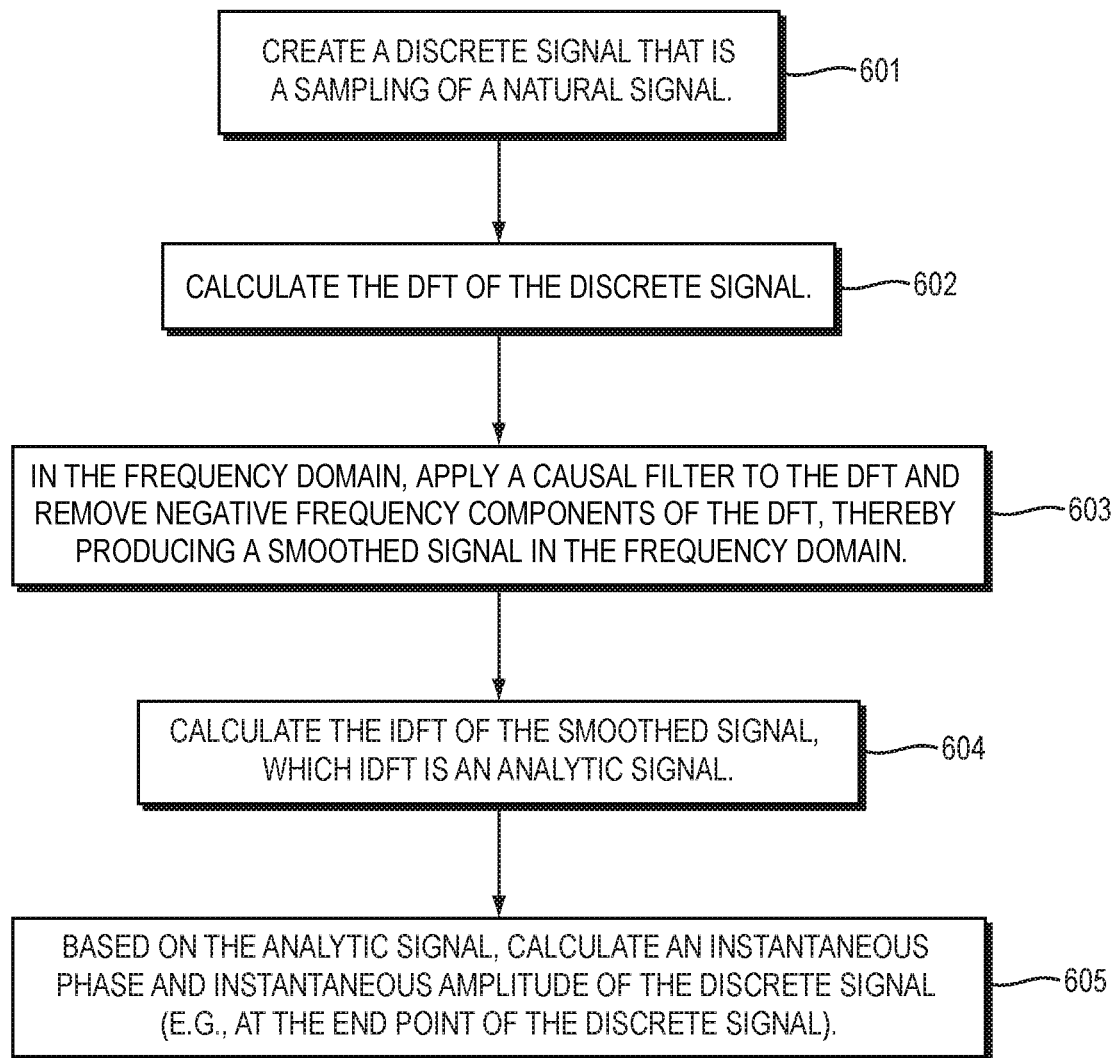
FIG. 6 shows a method of "frequency domain" ECHT (endpoint-corrected Hilbert transform).

FIG. 6 shows a method of "frequency domain" ECHT, in an illustrative implementation of this invention. In the example shown in FIG. 6, the method includes the following steps: Create a discrete signal that is a sampling of a natural signal (Step 601). Calculate the DFT of the discrete signal (Step 602). In the frequency domain, apply a causal filter to the frequency domain representation of the signal and remove negative frequency components of that representation, thereby producing a smoothed signal in the frequency domain (Step 603). Calculate the IDFT of the smoothed signal, which results in an analytic signal (Step 604). Based on the analytic signal, calculate an instantaneous phase and instantaneous amplitude of the discrete signal, such as at the end point of the discrete signal (Step 605).

In some cases where a "frequency domain smoothing" version of ECHT is employed, a computer calculates a smoothed signal in the frequency domain. The smoothed signal is the product of three signals: (1) the frequency domain representation of the impulse response of a causal filter, (2) what we call a "scrubber signal" (described in more detail below); and (3) the frequency domain representation of a discrete signal, which discrete single is a sampling of a natural signal of interest. Then the computer calculates an analytic signal, which is the IDFT of the smoothed signal. Then, based on the analytic signal, the computer calculates the instantaneous phase and amplitude of the natural signal.

The "scrubber signal" removes negative frequency components. Specifically, as used herein, a "scrubber signal" means a signal that, when multiplied by a frequency domain representation of a signal, removes negative frequency components from that frequency domain representation. Put differently, the product of a scrubber signal and a frequency domain representation of a signal is another frequency domain representation that does not have negative frequency components. C[n] (mentioned below) is an example of a "scrubber signal". Removing negative frequency components is desirable in the computation of an analytic signal, which has no negative frequency components.

In some cases, "frequency domain" ECHT involves causal filtering, in the frequency domain, of a spectral spread that results from a jump discontinuity between the two ends of a finite signal in the time domain.

In some cases, "frequency domain" ECHT reduces the spreading out of a spectrum that resulted from a jump discontinuity between the two ends of a finite signal in the time domain. This process of reducing the frequency spreading by reshaping the spectrum is effectively a filtering process.

In some cases, "frequency domain" ECHT includes the following steps:

Step A: Calculate $\hat{X}[n]$ as follows: $\hat{X}[n]=H[n]C[n]X[n]$, where

C[n] is:

$$C[n] = \begin{cases} 0 & n < 0 \\ 2 & 0 < n < \frac{N}{2} \\ 1 & n = 0, \frac{N}{2} \end{cases}$$

and where X[n] is the DFT (discrete Fourier transform) of a real-valued, discrete signal (for example, the discrete signal may comprise a sampled physiological signal, such as a sampled neural signal), and where H[n] is the DFT of h[n], and where h[n] is the impulse response of an LTI causal filter such that h[n]=0 for n<0, and where N is the sample size, and where n is an integer such that $$-\frac{N}{2} < n \le \frac{N}{2}.$$

Step B: Calculate an analytic signal $\hat{x}[n]$ as follows: $\hat{x}[n]=\text{IDFT}(\hat{X}[n])$, where IDFT is the inverse discrete Fourier transform operator.

Step C: Calculate the instantaneous amplitude A of the real-valued discrete signal x[n] and the instantaneous phase φ of the real-valued discrete signal x[n] as follows:

$$A[n] = \sqrt{\text{Re}\{\hat{x}[n]\}^2 + \text{Im}\{\hat{x}[n]\}^2}$$

$$\phi[n] = \text{atan}\left(\frac{\text{Im}\{\hat{x}[n]\}}{\text{Re}\{\hat{x}[n]\}}\right)$$

where Re{$\hat{x}$[n]} and Im{$\hat{x}$[n]} are the real portion and imaginary portion, respectively, of the complex analytic signal $\hat{x}$[n].

"End-Padded Time Domain" ECHT

In some cases, one or more computers (e.g., in a neuromodulator) correct the Gibbs phenomenon by performing what we call "end-padded time domain" ECHT.

In some cases, in "end-padded time domain" ECHT, the computer appends a segment of data values (e.g., zeros) of at least one period length to the end of the signal and then applies a causal filter, which has the directionality property, to make the padded signal continuous and differentiable at the endpoint of the original signal without deforming the original end of the signal. By pushing away the end of the padded signal from the original end before the DFT procedure, the computer ensures that the Gibbs distortion occurs away from the original end of the signal. This allows a computer to accurately compute instantaneous phase and instantaneous amplitude at t_now (the point in the analytic signal that corresponds in time to the end of the original signal).

Figure 7:
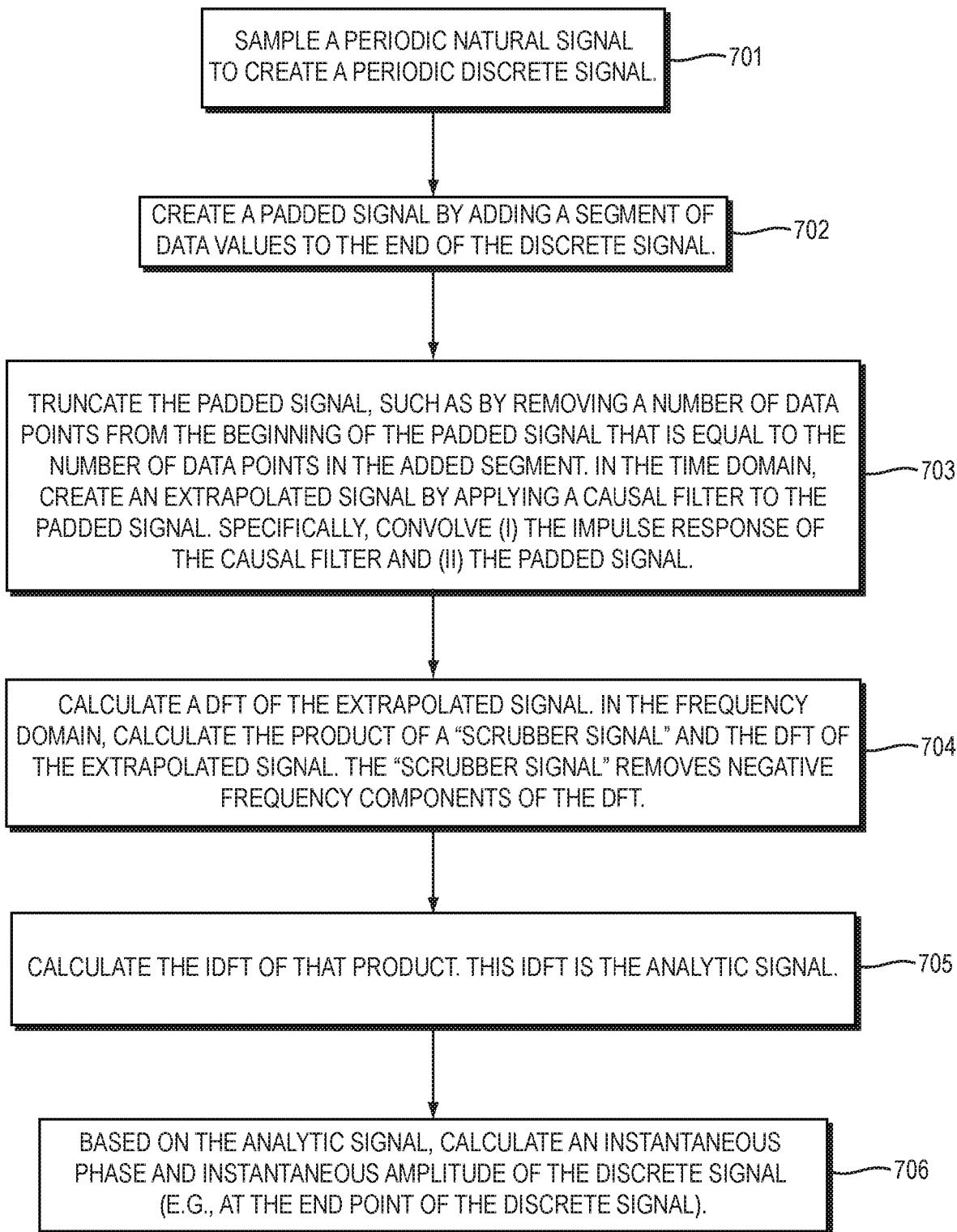
FIG. 7 shows a method of "end-padded time domain" ECHT.

FIG. 7 shows a method of "end-padded time domain" ECHT, in an illustrative implementation of this invention. In the example shown in FIG. 7, the method includes the following steps: Sample a periodic natural signal to create a periodic discrete signal (Step 701). Create a padded signal by adding a segment of data values to the end of the periodic discrete signal (Step 702). Truncate the padded signal, such as by removing, from the beginning of the padded signal, a number of data points that is equal to the number of data points in the added segment. In the time domain, create an extrapolated signal by applying a causal filter to the padded signal. Specifically, convolve (i) the impulse response of the causal filter and (ii) the padded signal (Step 703). Calculate a DFT of the extrapolated signal. In the frequency domain, calculate the product of a "scrubber signal" and the frequency domain representation of the extrapolated signal. Again, the "scrubber signal" removes negative frequency components (Step 704). Calculate the IDFT of that product. This IDFT is the analytic signal (Step 705). Based on the analytic signal, calculate the instantaneous phase and instantaneous amplitude of the natural signal. (Step 706).

In "end-padded time domain" ECHT, a padded discrete signal is created by adding a segment of data points at the end of a real-valued, discrete, periodic signal. The length of the added segment is greater than or equal to the length of a period of the original (unpadded) signal. The added segment may consist of zeroes. An advantage of zeroes is that they do not contain prior information. Alternatively, the added segment may include non-zero values. For example, the added segment may include a duplicate of the original signal or a portion of the original signal.

In "end-padded time domain" ECHT, the padded signal is casually smoothed. This may be done to smooth an abrupt transition that would otherwise be introduced by adding the extra data segment at the end (e.g., by zero padding at the end). For example, if the original signal is sinusoidal and it is zero padded by adding zeroes at the original end, then—in the absence of smoothing—a discontinuity would occur at the original end of the signal, where the padded signal transitions abruptly from a sinusoidal curve to a flat line of zeroes.

In "end-padded time domain" ECHT, casual smoothing is performed in the time domain, to prevent this problem. Specifically, the padded signal is causally smoothed, by convolving (i) the impulse response of a causal filter, and (ii) the padded signal. The causal filter smooths the padded signal, such that a discontinuity does not occur at the data point that was formerly the end of original signal.

In some cases, "end-padded time domain" ECHT includes the following steps:

Step A': Zero-pad a sample, which sample is a real-valued discrete signal x[n]. The zero-padding consists of adding zeros at the end of the sample. For example, x[n] may comprise a sampling of a natural signal (e.g., a neural signal or a muscle tremor).

Step B': Truncate the sample to sample size N.

Step C': Calculate a convolved signal x'[n]=h[n]*x[n], where h[n] is the impulse response of a causal filter such that h[n]=0 for n<0 and where "*" is convolution operator.

Step D': Calculate $\hat{X}[n]$ as follows: $\hat{X}[n]=C[n]X'[n]$, where

C[n] is:

$$C[n] = \begin{cases} 0 & n < 0 \\ 2 & 0 < n < \frac{N}{2} \\ 1 & n = 0, \frac{N}{2} \end{cases}$$

and where X'[n] is the DFT (discrete Fourier transform) of x'[n], N is the sample size (e.g., number of discrete sampled values in the sample), and n is an integer such that $$-\frac{N}{2} < n \leq \frac{N}{2}.$$

Step E': Calculate an analytic signal $\hat{x}[n]$ as follows: $\hat{x}[n]=\text{IDFT}(\hat{X}[n])$, where IDFT is the inverse discrete Fourier transform operator.

Step F': Calculate the instantaneous amplitude A of the real-valued discrete signal x[n] and the instantaneous phase φ of the real-valued discrete signal x[n] as follows:

$$A[n] = \sqrt{\text{Re}\{\hat{x}[n]\}^2 + \text{Im}\{\hat{x}[n]\}^2}$$

$$\phi[n] = \text{atan}\left(\frac{\text{Im}\{\hat{x}[n]\}}{\text{Re}\{\hat{x}[n]\}}\right)$$

where Re{$\hat{x}[n]$} and Im{$\hat{x}[n]$} are the real portion and imaginary portion, respectively, of the complex analytic signal $\hat{x}[n]$.

In the above example of "end-padded time domain" ECHT, Step B' (truncating) is optional and may be omitted. In some cases, Step B' (truncating) consists of removing the first half of the original signal by removing a number of data values, and Step A' (padding) consists of adding the same number of zeroes at the end of the original sample. Step B' (truncating) has at least two advantages: (a) it reduces the size of the sample window (which would otherwise increase due to the padding), and (b) results in a similar sample window as one would use with conventional Hilbert transform.

"Front-padded Time Domain" ECHT

In some implementations of this invention, one or more processors (e.g., in a neuromodulator) perform what we call "front-padded time domain" ECHT.

In some cases, "front-padded time domain" ECHT corrects the Gibbs phenomenon by ensuring that a signal will be continuous and differentiable at the original end of the signal when a replica of the signal is appended to the signal, as occurs in the DFT of a finite signal. In "front-padded time domain" ECHT, the neuromodulator front-pads a sample with a copy of an end segment of the sample, then applies a causal filter to the padded sample, and then removes the added segment in the time domain, prior to the DFT and IDFT steps. The correction is made before the IDFT step that results in an analytic signal. A computer selectively deforms the beginning of the sample in the time domain and does not deform the end of the sample. In "front-padded time domain" ECHT, the value of the end of the sample is not changed, but the value of the beginning of the sample is changed, such that the value of the signal at the beginning and end of the signal is the same. Thus, in some cases, if a replica of the sample is appended to the sample at the original end of the sample (as is done during the DFT of a finite sample), the padded sample is continuously differentiable at the original end of the sample. By removing the jump discontinuity at that point, a computer eliminates (or significantly reduces) the Gibbs phenomenon distortions at the end of the analytic signal that results from taking an IDFT. This allows a computer to accurately compute instantaneous phase and instantaneous amplitude at the end of the analytic signal (which corresponds in time to the end of the original sample). In "front-padded time domain" ECHT, the start and end values of the causally smoothed signal in the frequency domain are the same, and thus, after the IDFT, the start and end values of the Hilbert transform (which is the imaginary component of the analytic signal) are the same.

In these cases: (a) a signal that starts at t start is front-padded with a copy of an end segment of the signal, (b) then the padded signal is causally smoothed in the time domain, and (c) then the padded signal is truncated by removing the segment that was added. This procedure results in a modified signal that, like the original signal, starts at t start. The modified signal has the same value at its beginning point (t start) as at its end point. (This is because the causal smoothing distorts the beginning point of the original signal, such that it fits the added segment that was padded in front of it and which was a copy of the end segment).

Figure 8:
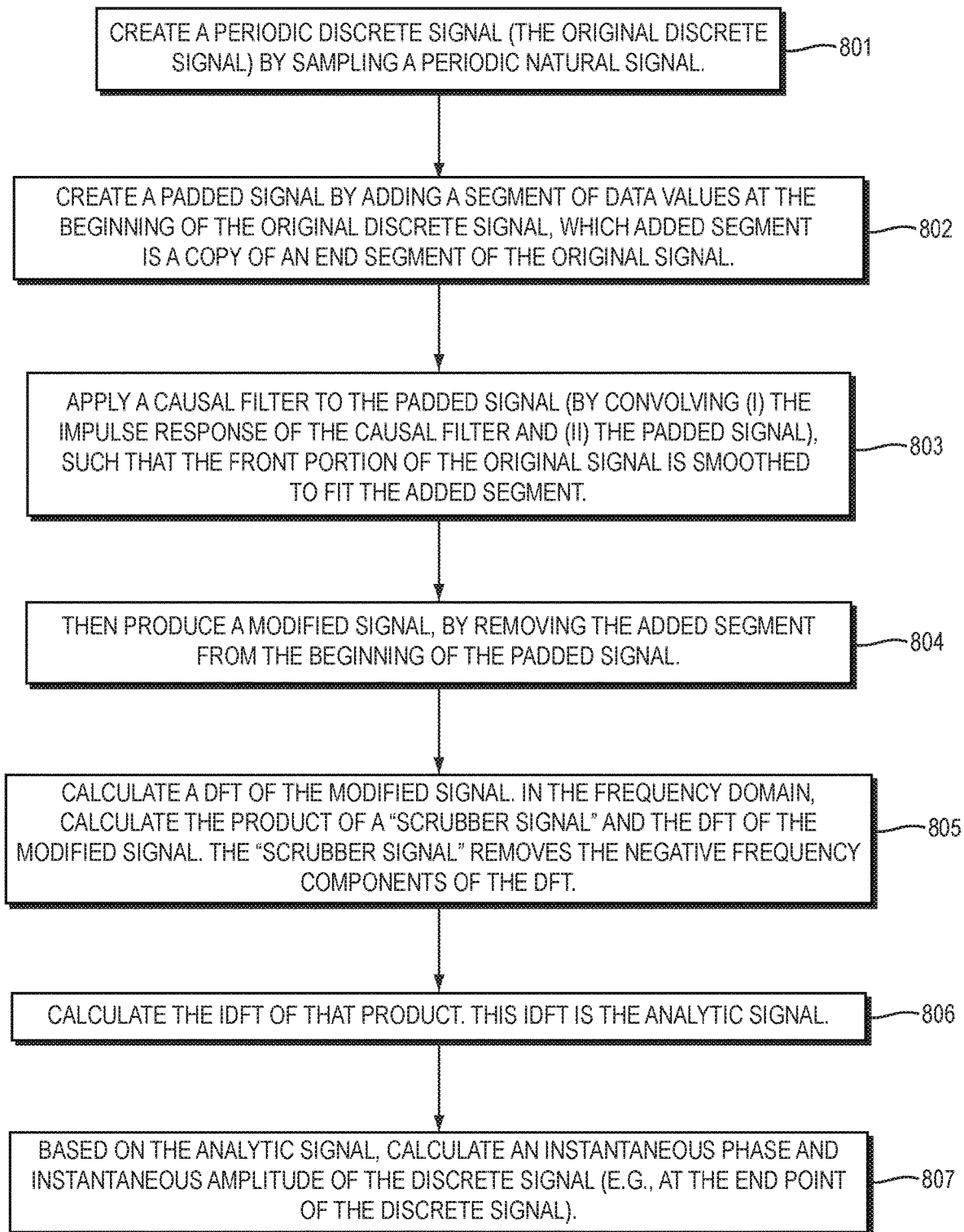
FIG. 8 shows a method of "front-padded time domain" ECHT.

FIG. 8 shows a method of "front-padded time domain" ECHT, in an illustrative implementation of this invention. In the example shown in FIG. 8, the method includes the following steps: Create a periodic discrete signal (the original discrete signal) by sampling a periodic natural signal (Step 801). Create a padded signal by adding a segment of data values at the beginning of the original discrete signal, which added segment is a copy of an end segment of the original signal (Step 802). Apply a causal filter to the padded signal (by convolving (i) the impulse response of the causal filter and (ii) the padded signal), such that the front portion of the original signal is smoothed to fit the added segment (Step 803). Then produce a modified signal, by removing the added segment (at the beginning of the padded signal) before the DFT is performed (Step 804). Calculate a DFT of the modified signal. In the frequency domain, calculate the product of a "scrubber signal" and the frequency domain representation of the modified signal. The "scrubber signal" removes negative frequency components of the frequency domain representation (Step 805). Calculate the IDFT of that product. This IDFT is the analytic signal (Step 806). Based on the analytic signal, calculate the instantaneous phase and instantaneous amplitude of the natural signal. (Step 807).

More Details Regarding ECHT

A common feature of all three methods discussed above—"frequency domain" ECHT, "end-padded time domain" ECHT, and "front-padded time domain" ECHT—is that a causal filter is applied to a signal. In each of these methods, the causal filter may comprise, for example, a causal IIR (infinite impulse response) filter or causal FIR (finite impulse response) filter. For instance, either the IIR filter or the FIR filter may comprise a causal Butterworth filter, causal Chebyshev filter or causal Bessel filter. The causal filter may be an LTI (linear and time-invariant) bandpass filter.

In some implementations of this invention, the causal filter: (a) reduces distortion of amplitude and phase of the signal inside a passband and (b) suppresses frequencies outside of the passband. The passband may be the range of frequencies of the natural signal.

Figure 9A:
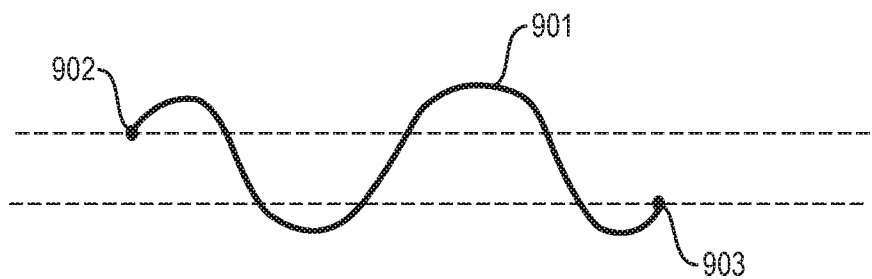
FIG. 9A shows a Hilbert transform signal that has different values at the start point and end point of the signal

FIG. 9A shows a Hilbert transform signal 901 that has different values at the start point 902 and end point 903 of the signal.

Figure 9B:
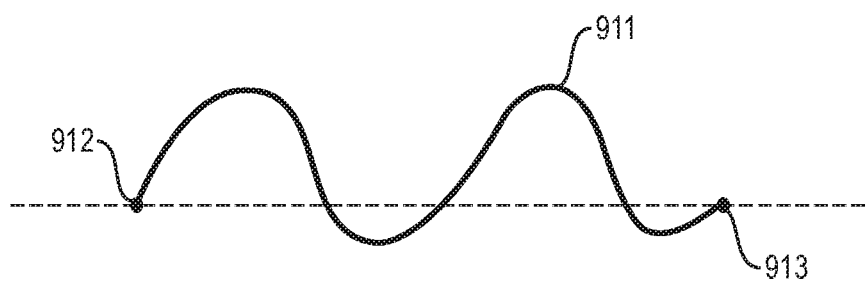
FIG. 9B shows a Hilbert transform signal that has the same values at the start point and end point of a signal.

FIG. 9B shows a Hilbert transform signal 911 that has the same values at the start point 912 and end point 913 of the signal.

In some cases in "frequency domain" ECHT, a causal filter is applied to the frequency domain representation of a signal, before the IDFT step. This correction in the frequency domain is such that the later IDFT step results in an analytic signal, in which the imaginary component (i.e., the Hilbert transform signal) has the same values at its start point and end point (such as the example shown in FIG. 9B).

In some cases in "front-padded time domain" ECHT, corrective steps are taken in the time domain, before the DFT/IDFT process. These corrective steps include (i) front-padding a discrete time signal (the original signal) with an added segment, which added segment is a copy of an end segment of the original discrete signal, (ii) then applying a causal filter that distorts the beginning of the original signal such that it fits the end of the added segment, and (iii) then removing the added segment. These corrective steps in the time domain are such that the later DFT/IDFT process results in an analytic signal, in which the imaginary component (i.e., the Hilbert transform signal) has the same values at its start point and end point (such as the example shown in FIG. 9B).

Figure 9C:
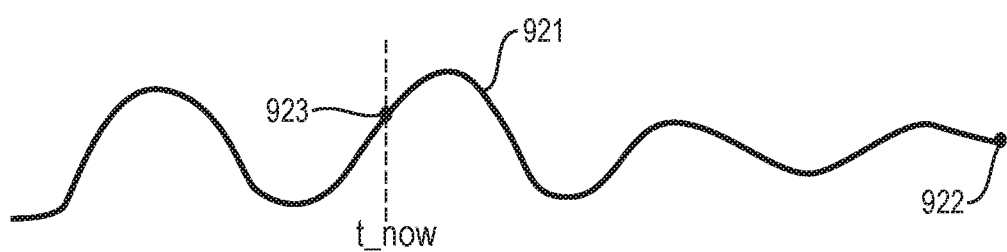
FIG. 9C shows a Hilbert transform signal in which the end of signal has been moved away from the original end of the sample, to a later point.

FIG. 9C shows a Hilbert transform signal 921 in which the end point 922 of signal has been moved away from t_now 923, in an illustrative implementation of this invention. T_now 923 is the point of the analytic signal (and of the Hilbert transform) that corresponds in time to the endpoint of the original discrete signal from which the analytic signal was derived.

In some cases in "end-padded time domain" ECHT, corrective steps are made in the time domain, before the DFT and IDFT steps. These corrective steps include (i) end-padding a discrete time signal (the original sample) with an added segment, such as a segment of zeroes, in order to produce a padded sample; and (ii) causal smoothing the padded sample. Due to an abrupt transition between the end of the original sample and the added segment, the causal filter produces ringing artifacts that smooth the added segment to fit the original sample. These corrective steps in the time domain result in an end-padded, casually smoothed time domain sample, in which the end point of the padded, smoothed sample is located at a distance from (and represents a point in time later than) the end point of the original sample. These corrective steps in the time domain are such that the later DFT/IDFT process results in a Hilbert transform signal in which the end point is at a distance from the end of the original sample (such as the example shown in FIG. 9C). The Hilbert transform is the imaginary part of the analytic signal.

Preferably, in "end-padded time domain" ECHT, the distance between the endpoint of the original sample (that is, t_now 923) and the end point 922 of the padded sample is equal to at least a period of the analytic signal. This causes the Gibbs effect to be insignificant at t_now. In some cases, the distance between t_now 923 and end point 922 is equal to at least three-quarters of a period of the analytic signal. The analytic signal has the same period as the original signal.

Advantageously, in illustrative implementations, ECHT allows a computer to accurately compute instantaneous phase over a selected range of frequencies. For example, in some cases, ECHT is accurate over a range of frequencies that is centered on, and equal in width to one half of, the main frequency of the natural signal. In some cases, the bandpass of the causal filter in ECHT is selected such that it is the same as that range of frequencies. For example, in some cases: (a) if the main frequency of the natural signal is 8 Hz, then ECHT is accurate in the range of 6-10 Hz; and (b) if the main frequency of the natural signal is known to be or measured as 8 Hz, the bandpass of the causal filter may be set to 6-10 Hz.

The ability to accurately measure instantaneous phase over a range of frequencies is helpful where the frequency of the natural signal being measured varies over time. For example, brain signals often have multiple time-varying frequencies with power-law distributions.

In FIGS. 10A-12E, the discrete increments of discrete signals are so small that the signals appear to be continuous. In FIGS. 10A, 10F, 11A, 11F and 12C, horizontal axis 1000 is time and the vertical axis 1010 is the value of the signal (e.g., volts, if the signal is a voltage signal).

FIGS. 10A to 10H illustrate aspects of a conventional method for determining instantaneous phase and amplitude of a natural signal. This conventional method is inaccurate because it does not correct for distortion due to the Gibbs phenomenon.

Figure 10A:
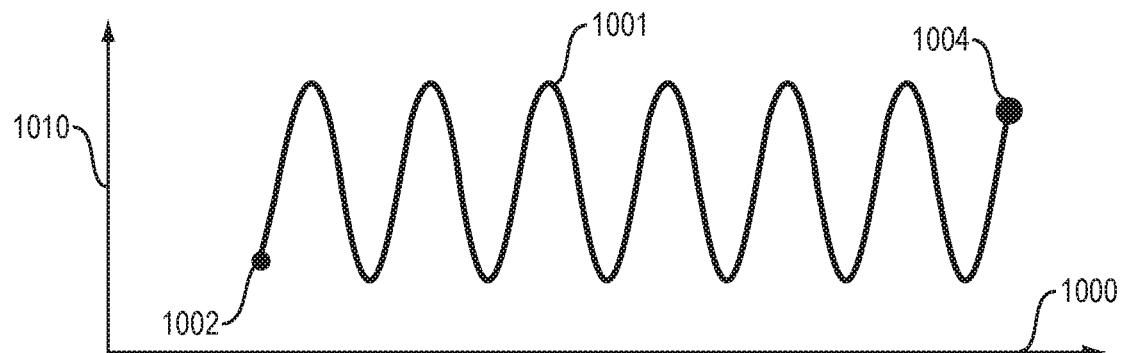
FIGS. 10A to 10H illustrate aspects of a conventional method for determining instantaneous phase and amplitude of a natural signal. This conventional method is inaccurate because it does not correct for distortion due to the Gibbs phenomenon. For this conventional method: (a)

For this conventional (prior art) method, FIG. 10A shows a discrete signal 1001 that is a sampling of a natural signal. Signal 1001 starts at start point 1002 and ends at end point 1004. FIG. 10A illustrates that signal 1001 differs in value at start point 1002 and end point 1004, and thus there is a jump discontinuity between these two points.

Figure 10B:
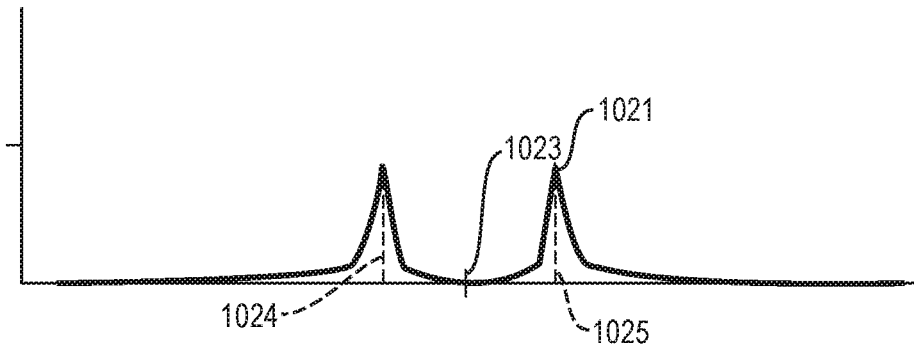
Figure 10C:
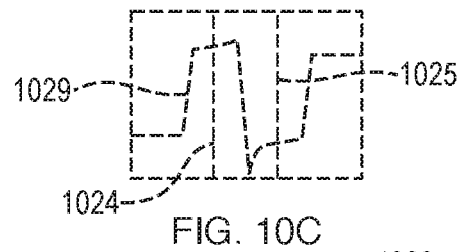
Figure 10D:
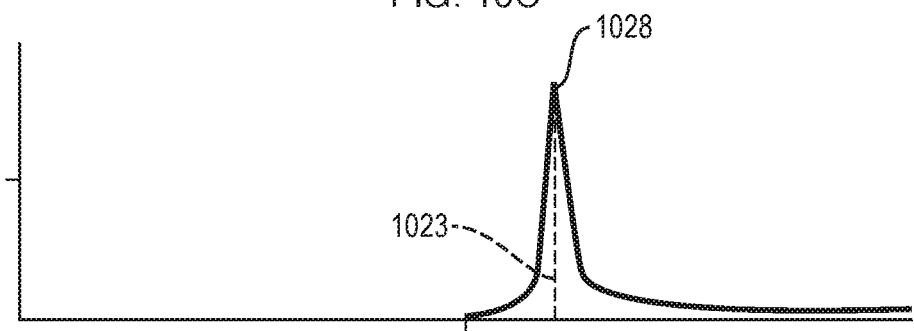
Figure 10E:
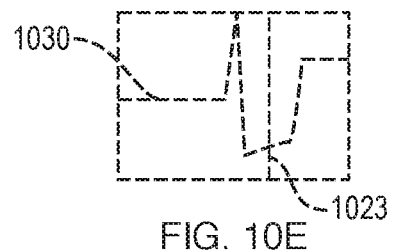

For this conventional method, FIG. 10B and FIG. 10C show the amplitude 1021 and phase 1029, respectively, of the Fourier transform of the discrete signal. FIG. 10D and FIG. 10E show the amplitude 1028 and phase 1030, respectively, of the Fourier transform of the analytic signal. These figures also show center frequency 1023. Frequencies 1024 and 1025 are equal to the center frequency plus or minus, respectively, half of the center frequency.

Figure 10F:
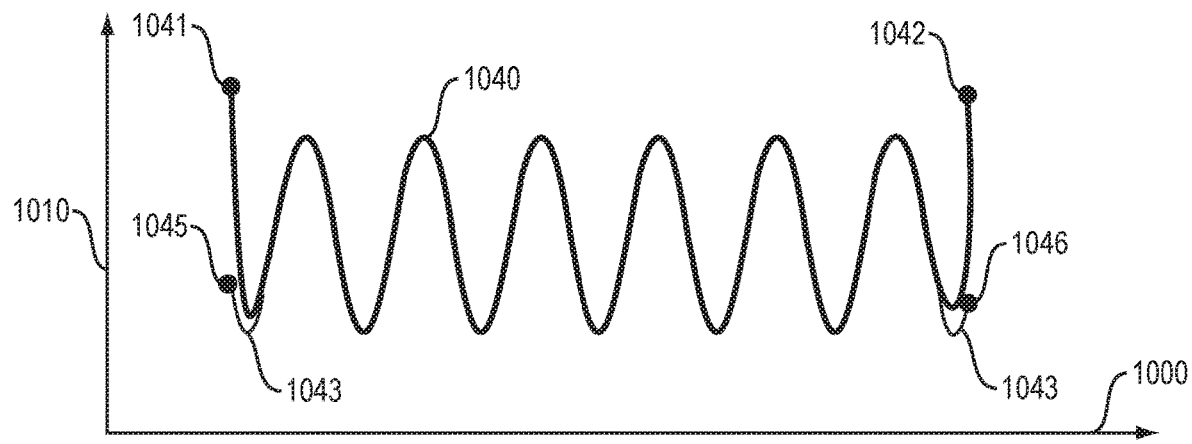

For this conventional method, FIG. 10F shows (a) the correct Hilbert transform signal 1043, which starts at start point 1045 and ends at end point 1046; and (b) the computed Hilbert transform signal 1040, which starts at start point 1041 and ends at end point 1042. Signals 1040 and 1043 overlap over much of their length.

Figure 10G:
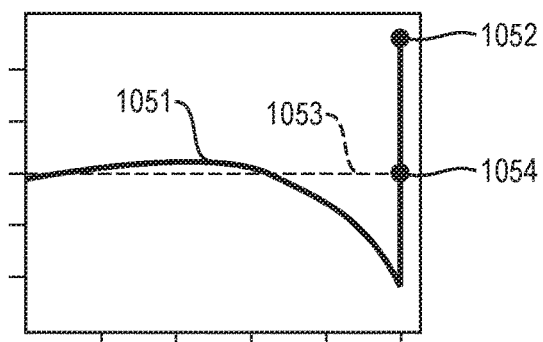

For this conventional (prior art) method, FIG. 10G shows the correct instantaneous amplitude A[n] values 1051 near their endpoint 1054 and the computed instantaneous amplitude A[n] values 1053 near their endpoint 1052. The large difference between the actual endpoint and computed endpoint indicates that instantaneous amplitude is not measured accurately at the end of the signal, in the conventional approach shown in FIG. 10G.

Figure 10H:
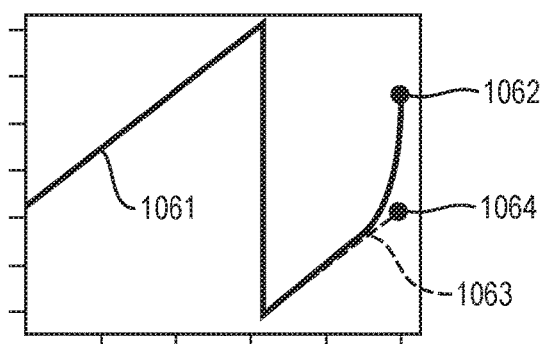

For this conventional (prior art) method, FIG. 10H shows the correct instantaneous phase φ[n] values 1063 near their endpoint 1064 and the computed instantaneous phase φ[n] values 1061 near their endpoint 1062. Curves 1061 and 1063 overlap over much of their length. The large difference between the actual endpoint and computed endpoint indicates that instantaneous phase is not measured accurately at the end of the signal, in the conventional approach shown in FIG. 10H.

FIGS. 11A to 11H illustrate aspects of an "end-padded time domain" version of ECHT, in an implementation of this invention. This version of ECHT accurately measures instantaneous phase and amplitude of a natural signal.

Figure 11A:
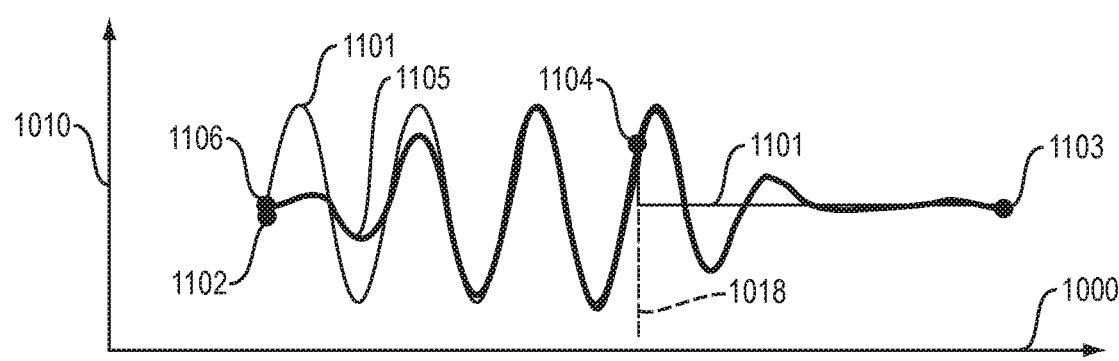
FIGS. 11A to 11H illustrate aspects of an "end-padded time domain" version of ECHT, in an implementation of this invention. This version of ECHT accurately measures instantaneous phase and amplitude of a natural signal. For this "end-padded time domain" version of ECHT: (a)

For this "end-padded time domain" version of ECHT, FIG. 11A shows a zero-padded signal before and after it is smoothed by a causal filter in the time domain (the "before" signal is 1101, the "after" signal is 1105) The signal is zero-padded after point 1004 which occurs at time t_now 1018. Signal 1101 starts at start point 1102 and ends at end point 1003. Signal 1105 starts at start point 1106 and ends at end point 1003.

Figure 11B:
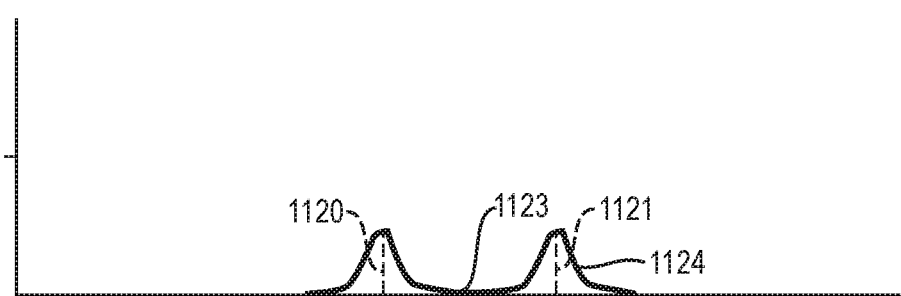
Figure 11C:
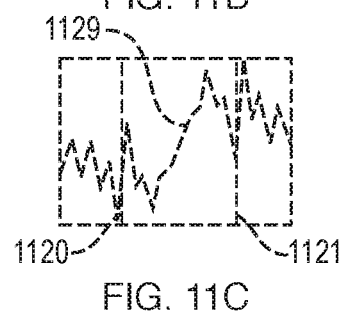
Figure 11D:
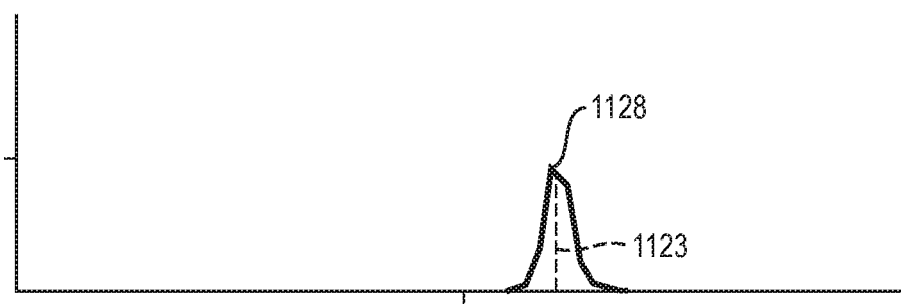
Figure 11E:
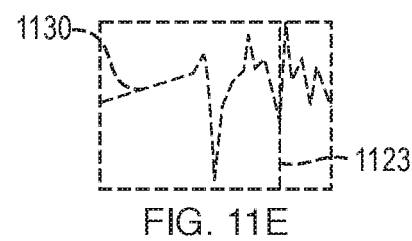

For this "end-padded time domain" version of ECHT, FIG. 11B and FIG. 11C show the amplitude 1124 and phase 1129, respectively, of the Fourier transform of the discrete signal. FIG. 11D and FIG. 11E show the amplitude 1128 and phase 1130, respectively, of the Fourier transform of the analytic signal. These figures also show center frequency 1123. Frequencies 1120 and 1121 are equal to the center frequency plus or minus, respectively, half of the center frequency.

Figure 11F:
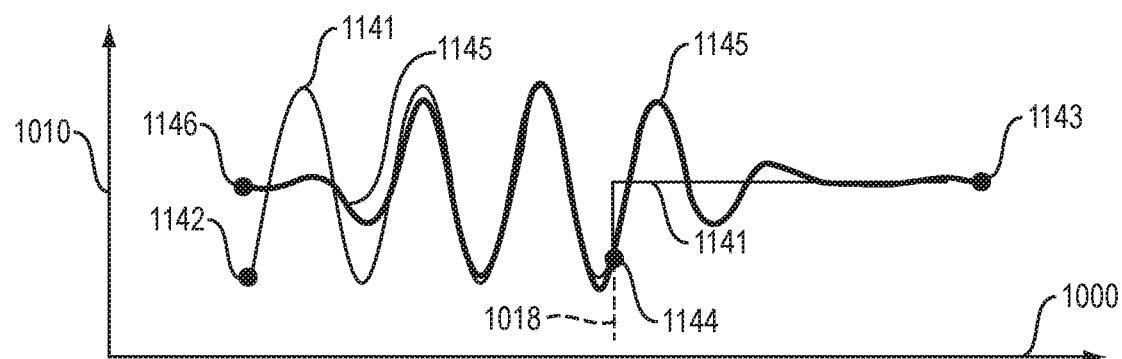

For this "end-padded time domain" version of ECHT, FIG. 11F shows (a) the correct Hilbert transform signal 1141, which starts at start point 1142 and ends at end point 1143; and (b) the computed Hilbert transform signal 1145, which starts at start point 1146 and ends at end point 1143. Signals 1141 and 1145 overlap in some areas. Point t_now 1144 is at time 1018 and corresponds in time to the end of the original signal, before zero-padding.

Figure 11G:
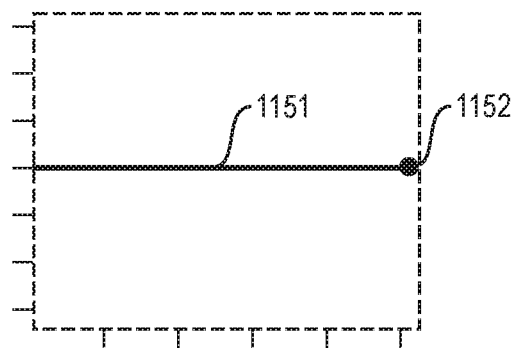
Figure 11H:
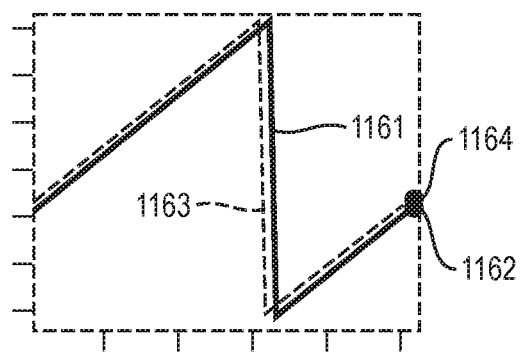

For this "end-padded time domain" version of ECHT, FIG. 11G shows correct instantaneous amplitude A[n]values 1151 near their endpoint 1152. The correct and computed instantaneous amplitude A[n] values overlap with each other, indicating that instantaneous amplitude is measured accurately near endpoint 1152, in "end-padded time domain" ECHT.

For this "end-padded time domain" version of ECHT, FIG. 10H shows the correct instantaneous phase φ[n] values 1163 near their endpoint 1164 and the computed instantaneous phase φ[n] values 1161 near their endpoint 1162. Curves 1161 and 1163 are close to each other over much of their length. This indicates that instantaneous phase is measured accurately near endpoint 1162, in "end-padded time domain" ECHT.

FIGS. 12A to 12E illustrate aspects of a "frequency domain" version of ECHT, in an implementation of this invention. This version of ECHT accurately measures instantaneous phase and amplitude of a natural signal.

Figure 12A:
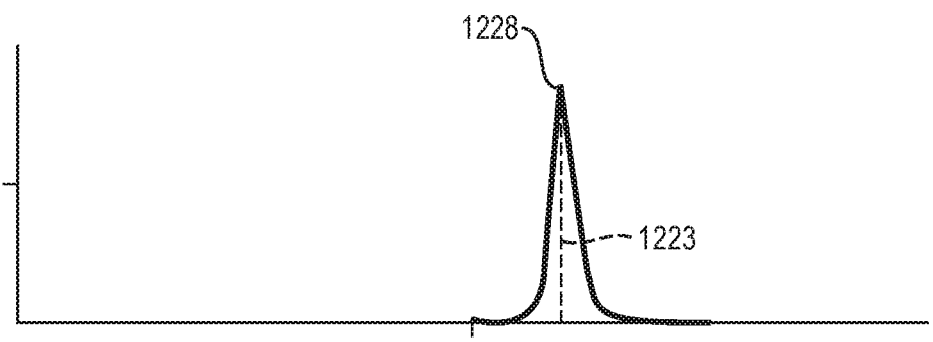
FIGS. 12A to 12E illustrate aspects of a "frequency domain" version of ECHT, in an implementation of this invention. This version of ECHT accurately measures instantaneous amplitude and phase of a natural signal. For this "frequency domain" version of ECHT: (a)
Figure 12B:
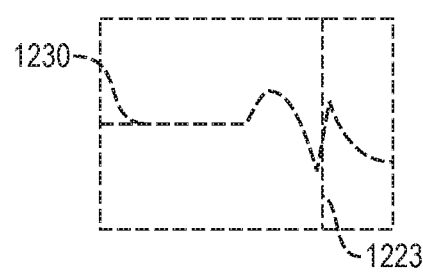

For this "frequency domain" version of ECHT, FIG. 12A and FIG. 12B show the amplitude 1228 and phase 1230, respectively, of the Fourier transform of the analytic signal. These figures also show center frequency 1223.

Figure 12C:
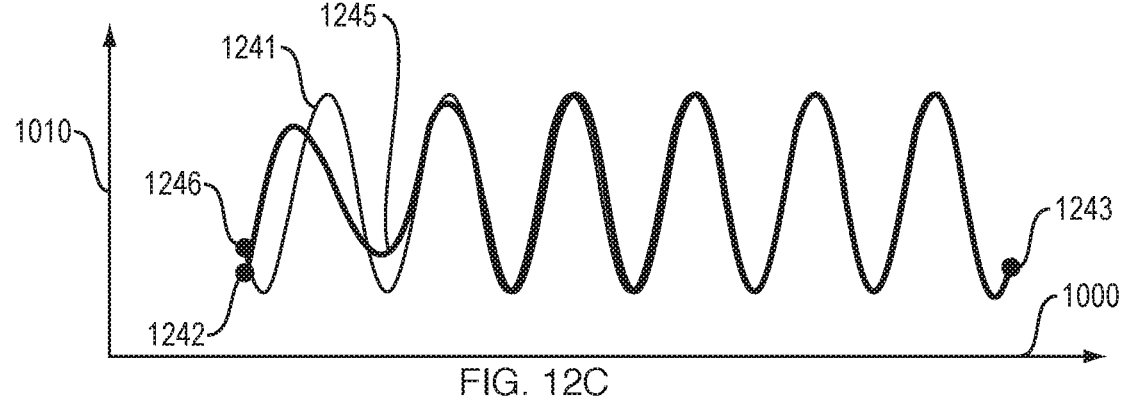

For this "frequency domain" version of ECHT, FIG. 12C shows (a) the correct Hilbert transform signal 1241, which starts at start point 1242 and ends at end point 1243; and (b) the computed Hilbert transform signal 1245, which starts at start point 1246 and ends at end point 1243. Signals 1241 and 1245 overlap in some areas.

Figure 12D:
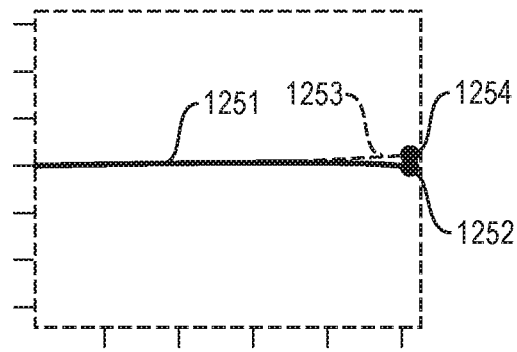

For this "frequency domain" version of ECHT, FIG. 12D shows correct instantaneous amplitude A[n] values 1253 near their endpoint 1254, and shows computed instantaneous amplitude values A[n] 1251 near their endpoint 1252. The correct and computed instantaneous amplitude A[n] values overlap with or are close to each other, indicating that instantaneous amplitude is measured accurately near endpoint 1252, in "frequency domain" ECHT.

Figure 12E:
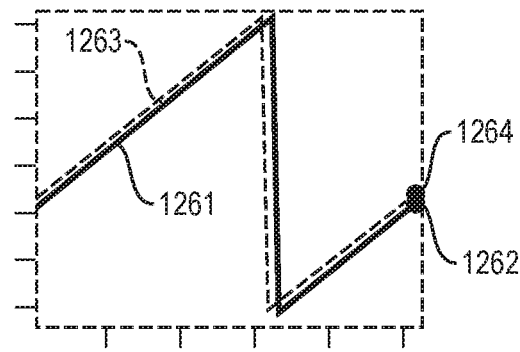

For this "frequency domain" version of ECHT, FIG. 12E shows the correct instantaneous phase φ[n] values 1263 near their endpoint 1264 and the computed instantaneous phase φ[n] values 1261 near their endpoint 1262. Curves 1261 and 1263 are close to each other. This indicates that instantaneous phase is measured accurately near endpoint 1262, in "frequency domain" ECHT.

In illustrative implementations of this invention, ECHT is not limited to measuring a physiological signal that is indicative of neural tissue activity. Instead, ECHT may be used to accurately measure, in real-time, the instantaneous phase and the instantaneous amplitude of any signal, including any physiological signal, or any seismological signal. For example, the signal that is processed by ECHT may comprise measurements taken by any sensor, including any electrical sensor (e.g., EEG sensor, ECG sensor, voltmeter, or current sensor), motion sensor (e.g., gyroscope, accelerometer or inertial measurement unit) magnetic sensor, light sensor, optical sensor, camera, acoustic sensor (e.g., microphone, geophone, hydrophone), pressure sensor, proximity sensor, or chemical sensor.

More Detail on Neuromodulation

As used herein, to say that a first signal is "phase-locked" with a second signal means that the phase of the first signal is equal to the phase of the second signal.

As used herein, to say that a first signal is "phase-difference-locked" with a second signal means that the difference between the phase of the first signal and the phase of the second signal is constant. For example, two signals that are anti-phasic relative to each other (i.e., 180 degrees in phase apart from each other) are "phase-difference-locked".

As used herein, to say that a first signal is "phase-coordinated" with a second signal means that the full width at half maximum (FWHM) of a histogram is less than 0.314159 radians, where (i) the histogram is a histogram of the difference, in radians, between (A) the instantaneous phase of the first signal and (B) the instantaneous phase of a shifted version of the second signal, which shifted version is shifted to the extent needed to cause the first signal and shifted signal to have the same phase at the first point in time that is taken into account in the histogram. Thus, loosely speaking, when a first and second signal are "phase-coordinated", the variation in difference in phase between the first and second signals is limited and the drift of the first and second signals relative to each other is limited.

Figure 13:
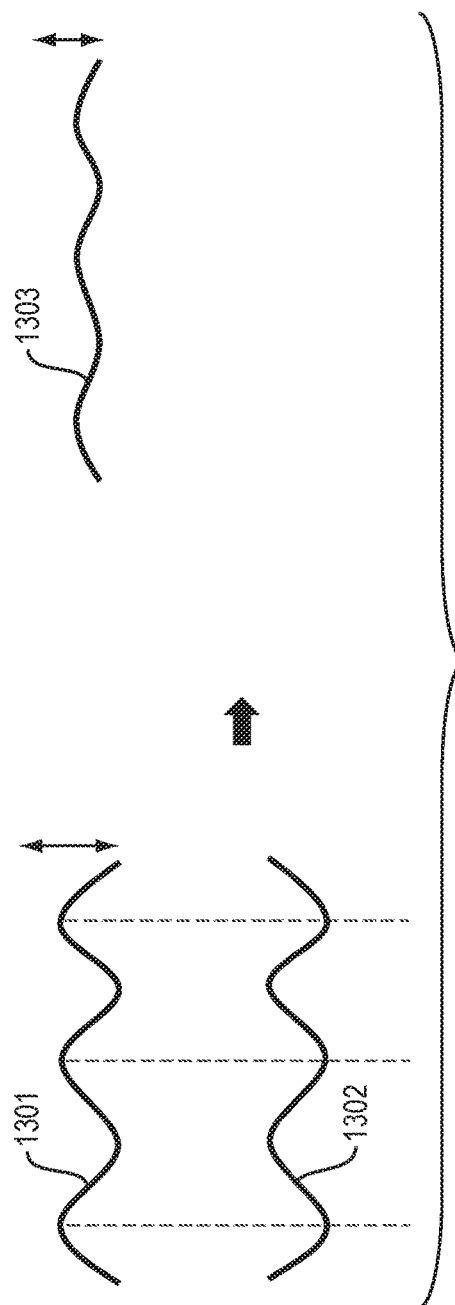
FIG. 13 shows a therapeutic signal that reduces the amplitude of a physiological signal.

FIG. 13 shows a therapeutic signal 1302 that is anti-phasic to a physiological signal 1301, in an illustrative implementation of this invention. This reduces the amplitude of physiological signal 1301, resulting in physiological signal 1303.

Figure 14:
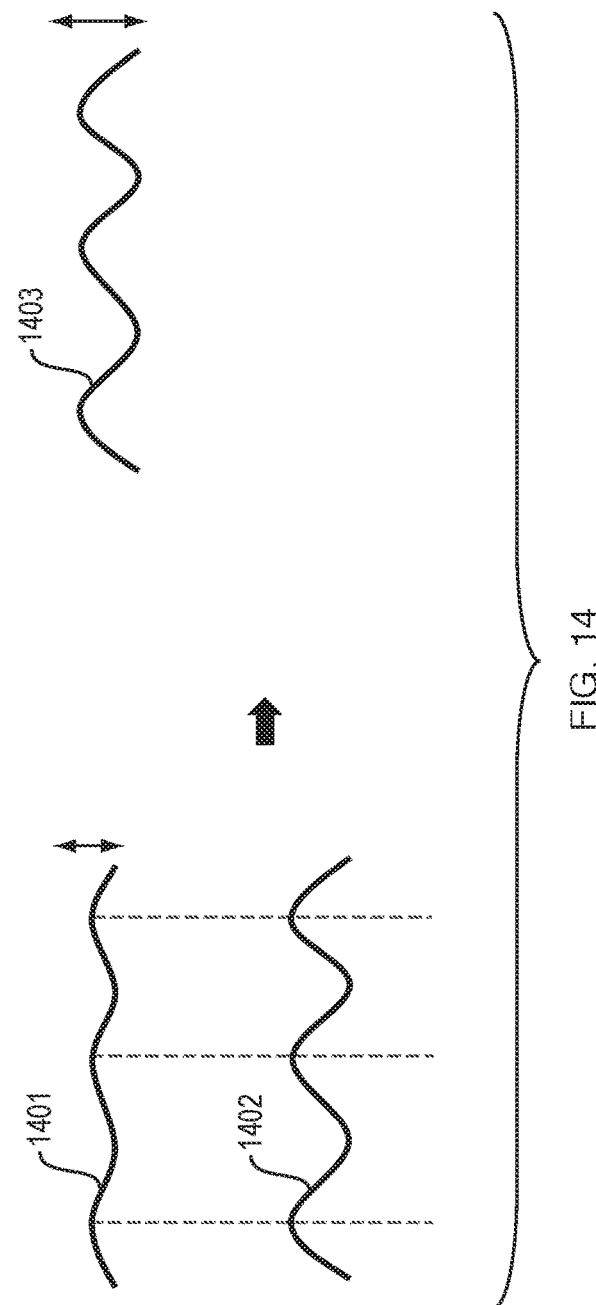
FIG. 14 shows a therapeutic signal that increases the amplitude of a physiological signal.

FIG. 14 shows a therapeutic signal 1402 that is phase-locked with a physiological signal 1401, in an illustrative implementation of this invention. This reduces the amplitude of physiological signal 1401, resulting in physiological signal 1403.

Figure 15:
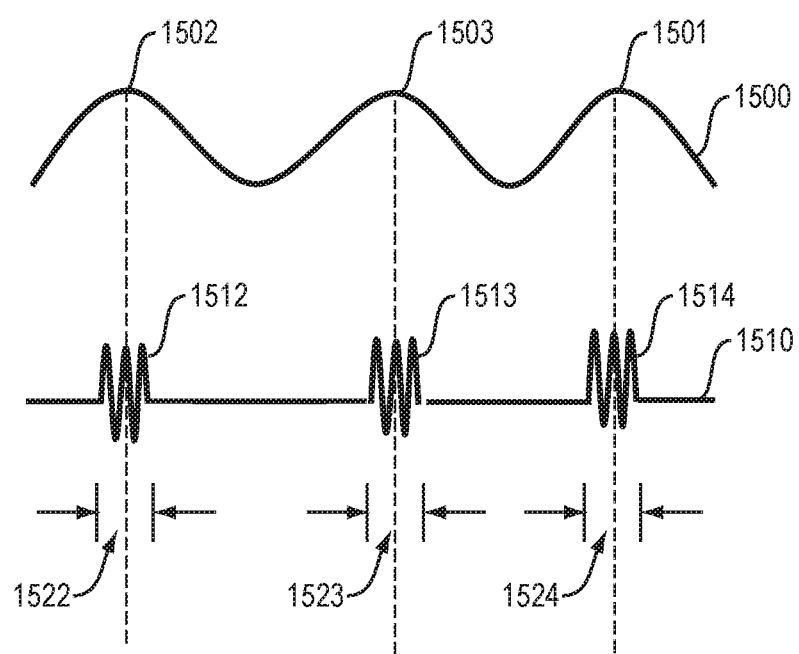
FIG. 15 shows an example of phase coding.

FIG. 15 shows an example of phase coding, in an illustrative implementation of this invention. In FIG. 15, a therapeutic signal 1510 includes short bursts 1512, 1513, 1514 that are phase-locked with a physiological signal 1500. These short bursts at high frequency occur only during a narrow phase range, e.g., 1522, 1523, 1524, of each period of the physiological signal 1500. In the example shown in FIG. 15, these short bursts occur at the peaks 1502, 1503, 1501 of the physiological signal 1500.

In FIGS. 13, 14 and 15, each therapeutic signal (1302, 1402, 1510) is phase-coordinated with the physiological signal (1301, 1401, 1500, respectively)

Source Code

The following is a description of the twelve ASCII text files (collectively, the "Source Code") listed in the Computer Program Listing section above.

Together, the Source Code comprises software for an ECHT algorithm. The Source Code is written in such a manner that it may be run on an Arduino Due embedded robotics controller, and may be compiled and loaded using Arduino IDE version 1.6.7.

The names of the twelve ASCII files have been modified (a) by replacing each period with an underscore, and (b) by appending the ".txt" extension to each file name. (These modifications were made in order to be able to upload the .txt files to the United States Patent & Trademark Office website during the patent application process). However, in order for the Source Code to run on the Arduino IDE version 1.6.7, these modifications to the file names need to be reversed, that is: (a) ".txt" would be removed from the end of the file names of the twelve ASCII text files; and (b) each underscore in the file names would be replaced by a period.

ECHT_ino.txt includes the main entry point for the software program set forth in the Source Code. Specifically, ECHT_ino includes the functions "setup( )" and "loop( )". (In this Arduino environment, the "setup( )" and "loop( )" functions replace a traditional "main( )" function. "setup( )" runs once at the start of the program. "loop( )" runs repeatedly thereafter).

The ECHT_ino.txt program reads an 0-3.3V analog signal being fed into the Arduino Due's ADC ports. This analog signal represents a physiological signal that is measured by one or more sensors. The ECHT_ino.txt program runs an ECHT algorithm, and uses both the Arduino's serial port and DAC ports to output a signal generated based on the ECHT estimated phase and amplitude. Endpoint correction is performed during execution of the ECHT_ino.txt program In the ECHT_ino.txt program, incoming sensor data is sampled from ADC ports "A0", "A1", and "A2". These three values are averaged and added as a newest sample point to a moving window. The ECHT algorithm is then applied to this window: The data is first bandpass filtered through a Butterworth filter. An efficient Hilbert transform, which uses a pair of integer-based FFT implementations, computes the analytic signal. The phase and amplitude are computed from the real and imaginary components of this analytic signal. Finally, an output or "generated" signal is produced which is a function of the instantaneous phase and amplitude computed by ECHT.

In the ECHT_ino.txt program, the serial port continuously streams four values: (1) mode (i.e., whether the system is in calibration mode or normal operating mode); (2) the sampling time; (3) incoming analog voltage; and (4) the generated signal. The DAC port outputs the generated signal as an analog voltage that varies from 0-3.3V. This analog voltage signal may control a voltage-controlled current source (VCCS) in a neuromodulator, and the VCCS may in turn output a neuromodulation current. Since the ECHT algorithm accurately computes the phase and amplitude of the incoming ADC signal, the amplitude and phase of the generated signal may be accurately controlled (e.g., by scaling, shifting or inverting). In addition, the Arduino serial port outputs the generated signal in a digital format, such that its values may be read out and analyzed.

FFT_C.txt is an implementation of the Fast Fourier Transform that uses floating point math. ECHT_ino.txt uses the precision of floating point math during "calibration" to estimate the central frequency of the incoming signal. A bandpass filter that is an element of ECHT may use this central frequency to more accurately filter the incoming signal.

FFT_H.txt is the header file for FFT.C.txt.

ButterworthBandpass_h.txt implements a Butterworth Bandpass filter, and bandpass filters the incoming signal.

liir_c.txt computes the Infinite Impulse Response (IIR) filter coefficients used by the Butterworth Bandpass filter. By allowing the filter coefficients to change, the bandpass filter may be modified to allow frequencies of interest to pass through while suppressing noise.

iir_h.txt is the header file for liir.c.txt

VarSizeSplitRadixRealP_cpp.txt is efficient integer implementation of FFT that works on signals with only real components. The FFT-based Hilbert transform starts with a FFT, then a frequency domain modification of the Fourier coefficients, and finally an inverse FFT to recover the analytic signal. This file (VarSizeSplitRadixRealP_cpp.txt) implements the starting FFT.

VarSizeSplitRadixRealP_h.txt is the header file for VarSizeSplitRadixRealP_cpp.txt VarSizeRadix4_cpp.txt is an efficient integer implementation of FFT that works on complex signals, signals with real and imaginary components. The FFT-based Hilbert transform starts with a FFT, then a frequency domain modification of the Fourier coefficients, and finally an inverse FFT to recover the analytic signal. This file (VarSizeRadix4_cpp.txt) implements an inverse FFT.

VarSizeRadix4_h.txt is the header file for VarSizeRadix4_cpp.txt waveconst_h.txt is an array-based, integer representation of a sine wave, and is used in place of the traditional "sin( )" function, which is slower to compute.

window_h.txt implements a moving/sliding window, and is used to cache samples so that the ECHT algorithm may process a window of samples during each invocation.

This invention is not limited to the software set forth in the twelve ASCII text files listed in the Computer Program Listing section above. Depending on the particular implementation, the software used in this invention may vary.

Computers

In exemplary implementations of this invention, one or more electronic computers (e.g., servers, network hosts, client computers, integrated circuits, microcontroller, controllers, field-programmable-gate arrays, personal computers, or other onboard or remote computers) are programmed and specially adapted: (1) to control the operation of, or interface with, hardware components of a neuromodulator, including any transducer or sensor; (2) to control the operation of, or interface with, hardware components of any sensor; (3) to perform any calculation to correct distortion due to Gibbs phenomenon, including to perform any "frequency domain" ECHT algorithm, "end-padded time domain" ECHT algorithm, or any "front-padded time domain" ECHT; (4) to control a transducer such that the transducer outputs a first signal that is phase-coordinated with a second signal; (5) to perform any other calculation, computation, program, algorithm, or computer function described or implied above; (6) to receive signals indicative of human input; (7) to output signals for controlling transducers for outputting information in human perceivable format; or (8) to process data, to perform computations, to execute any algorithm or software, and to control the read or write of data to and from memory devices (items 1-8 of this sentence referred to herein as the "Computer Tasks"). The one or more computers (e.g., 201) communicate with each other or with other components of the system either: (a) wirelessly, (b) by wired connection, (c) by fiber-optic link, or (d) by a combination of wired, wireless or fiber optic links.

In exemplary implementations, one or more computers (e.g., 201) are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers (e.g., 201) execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Network Communication

In illustrative implementations of this invention, one or more electronic devices are configured for wireless or wired communication with other electronic devices in a network.

For example, in some cases, there are multiple devices in a network. Each of the devices may include a wireless communication module for wireless communication with other electronic devices in a network. Each wireless communication module may include (a) one or more antennas, (b) one or more wireless transceivers, transmitters or receivers, and (c) signal processing circuitry. The wireless communication module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, computer port, cables or wiring.

In some cases, one or more computers (e.g., 210) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Definitions

The terms "a" and "an", when modifying a noun, do not imply that only one of the noun exists.

To compute "based on" specified data means to perform a computation that takes the specified data as an input.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

As used herein, to say that a discrete signal is "continuous" and "differentiable" at a given point means that a second, continuous, signal exists such that: (a) the second signal is differentiable and continuous at the given point; and (b) the values and spectrum of the discrete signal approximate the values and spectrum of the second signal.

To "correct" means (i) to correct, (ii) to prevent, (iii) to mitigate or ameliorate, or (iv) to compensate for. A non-limiting example of correcting a distortion is to compensate for the distortion before, after or concurrently with the distortion.

To say that a first data point of a first signal "corresponds in time" to a second data point of a second signal means that the first and second data points are associated with the same moment in time. For example, if a first signal is x(t) and a second signal is y(t), where t is time, and both signals start at the same time and have the same unit of time, then x(3) and y(3) "correspond in time" to each other.

"Defined Term" means a term or phrase that is set forth in quotation marks in this Definitions section.

To say that a second point of a signal is "later" than a first point of the signal means that the second point is closer to the endpoint of the signal than the first point is.

For an event to occur "during" a time period, it is not necessary that the event occur throughout the entire time period. For example, an event that occurs during only a portion of a given time period occurs "during" the given time period.

The term "e.g." means for example.

To "end-pad" a signal which has a given point that is the endpoint of the signal means to add one or more data values to the signal after the given point, such that the given point is no longer the endpoint of the signal.

The "endpoint" of a discrete signal means the final data value in the signal.

An "end-segment" of a discrete signal means a segment of the signal that includes the endpoint of the signal.

The fact that an "example" or multiple examples of something are given does not imply that they are the only instances of that thing. An example (or a group of examples) is merely a non-exhaustive and non-limiting illustration.

To "filter" a signal or to "apply a filter" to a signal includes: (a) to digitally apply a filter to the signal in the time domain, by convolving (i) an impulse response of the filter and (ii) the signal; (b) to digitally apply a filter to the signal in the Fourier frequency domain, by multiplying (i) a Fourier transform of the impulse response of the filter and (ii) a Fourier transform of the signal; or (c) to filter the signal with an analog filter.

To "apply a causal filter" or to "casually filter" or to "casually smooth" a signal includes (a) to reverse the order of data values in the signal, such that the start of the signal becomes the end of the signal and the end of the signal becomes the start of the signal, and then (b) to apply an anti-causal filter to the reversed signal. Likewise, any description of an algorithm that involves applying a causal filter shall be construed as also describing an alternative version in which: (a) the signal is reversed and an anti-causal filter is applied, as described in the preceding sentence; and (b) the algorithm is modified, mutatis mutandis, to accommodate the reversed order, such as, for example, by replacing end-padding with front-padding.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

To "front-pad" a signal which has a given point that is the start point of the signal means to add one or more data values to the signal before the given point, such that the given point is no longer the start point of the signal.

A "front-segment" of a discrete signal means a segment of the signal that includes the start point of the signal.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"LTI" means linear and time-invariant.

To "multiply" includes to multiply by an inverse. Thus, to "multiply" includes to divide.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

The term "phase-locked" is defined elsewhere in this document.

The term "phase-locked" is defined elsewhere in this document.

The term "phase-coordinated" is defined elsewhere in this document.

As used herein, the term "set" does not include a group with no elements. Mentioning a first set and a second set does not, in and of itself, create any implication regarding whether or not the first and second sets overlap (that is, intersect).

"Some" means one or more.

As used herein, a "subset" of a set consists of less than all of the elements of the set.

The "start point" of a discrete signal means the beginning data value in the signal.

The term "such as" means for example.

The term "time t_now" is merely a way to identify a particular time, such that the particular time or data point may be referred to with specificity later. For example, "t_now" may in some cases be a past or present moment in time that is being identified, so that it may be referred to with specificity later. A "point t_now" is a data point of a signal, which data point is the value of the signal at time t_now.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, the Applicant or Applicants are acting as his, her, its or their own lexicographer.

Variations

This invention may be implemented in many different ways. Here are some non-limiting examples:

In some implementations, this invention is a method comprising, in combination: (a) a sensor taking measurements of a periodic physiological signal, which physiological signal is indicative of activity of neural tissue; (b) one or more computers performing calculations that include (i) computing a periodic discrete signal, which periodic discrete signal comprises a sampling of the measurements, (ii) based on the periodic discrete signal, computing a Hilbert transform and an analytic signal, the Hilbert transform being the imaginary component of the analytic signal, (iii) based on the analytic signal, computing an instantaneous phase at the end point of the analytic signal, (iv) based on the instantaneous phase, outputting instructions; and (c) one or more transducers outputting, based on the instructions, a signal that affects the activity of neural tissue; wherein (1) the Hilbert transform has a point, t_now, that corresponds in time to the end of the periodic discrete signal, and (2) the Hilbert transform ends at t_now and the value of the Hilbert transform at t_now is equal to the value of the Hilbert transform at the start point of the Hilbert transform. In some cases, the physiological signal is an electrical signal. In some cases, physiological signal is motion caused by a physiological tremor. In some cases, the calculations include computing a discrete Fourier transform of the periodic discrete signal and then applying a causal filter to the discrete Fourier transform. In some cases, the calculations include: (a) front-padding the periodic discrete signal with a copy of an end segment of the periodic discrete signal to create a padded signal; (b) then applying a causal filter to the padded signal; and (c) then removing a front segment of the padded signal. In some cases, the signal that affects the activity of neural tissue is phase-coordinated with the physiological signal. Each of the cases described above in this paragraph is an example of the method described in the first sentence of this paragraph, and is also an example of an embodiment of this invention that may be combined with other embodiments of this invention.

In some implementations, this invention is an apparatus comprising: (a) a sensor for taking measurements of a physiological signal, which physiological signal is indicative of activity of neural tissue; (b) one or more computers that are programmed to perform calculations that include (i) computing a periodic discrete signal, which periodic discrete signal comprises a sampling of the measurements, (ii) based on the periodic discrete signal, computing a Hilbert transform and an analytic signal, the Hilbert transform being the imaginary component of the analytic signal, (iii) based on the analytic signal, computing an instantaneous phase at the end point of the analytic signal, (iv) based on the instantaneous phase, outputting instructions; and (c) one or more transducers for outputting, based on the instructions, a signal that affects the activity of neural tissue; wherein (1) the Hilbert transform has a point, t_now, that corresponds in time to the end of the periodic discrete signal, and (2) the Hilbert transform ends at t_now and the value of the Hilbert transform at t_now is equal to the value of the Hilbert transform at the start point of the Hilbert transform. In some cases, the physiological signal is an electrical signal. In some cases, the physiological signal is motion caused by a physiological tremor. In some cases, the calculations include computing a discrete Fourier transform of the periodic discrete signal and then applying a causal filter to the discrete Fourier transform. In some cases, the calculations include: (a) front-padding the periodic discrete signal with a copy of an end segment of the periodic discrete signal to create a padded signal; (b) then applying a causal filter to the padded signal; and (c) then removing a front segment of the padded signal. In some cases, the signal that affects the activity of neural tissue is phase-coordinated with the physiological signal. Each of the cases described above in this paragraph is an example of the apparatus described in the first sentence of this paragraph, and is also an example of an embodiment of this invention that may be combined with other embodiments of this invention.

In some implementations, this invention is a method comprising, in combination: (a) a sensor taking measurements of a physiological signal, which physiological signal is indicative of activity of neural tissue; (b) one or more computers performing calculations that include (i) computing a periodic discrete signal, which periodic discrete signal comprises a sampling of the measurements, (ii) based on the periodic discrete signal, computing a Hilbert transform and an analytic signal, the Hilbert transform being the imaginary component of the analytic signal, (iii) based on the analytic signal, computing instantaneous phase of the analytic signal, (iv) based on the instantaneous phase, outputting instructions; and (c) one or more transducers outputting, based on the instructions, a signal that affects the activity of neural tissue; wherein (1) the Hilbert transform has a point, t_now, that corresponds in time to the end of the periodic discrete signal, (2) the Hilbert transform ends later than t_now, at a distance from t_now that is equal to at least three-quarters of the period of the periodic discrete signal, and (3) the calculations include end-padding the periodic discrete signal to produce a padded signal and then smoothing the padded signal with a causal filter that introduces ringing artifacts into the padded signal. In some cases, the physiological signal is an electrical signal. In some cases, the physiological signal is motion caused by a physiological tremor. In some cases, the signal that affects the physiological signal is phase-coordinated with the physiological signal. Each of the cases described above in this paragraph is an example of the method described in the first sentence of this paragraph, and is also an example of an embodiment of this invention that may be combined with other embodiments of this invention.

In some implementations, this invention is an apparatus comprising: (a) a sensor for taking measurements of a physiological signal, which physiological signal is indicative of activity of neural tissue; (b) one or more computers that are programmed to perform calculations that include (i) computing a periodic discrete signal, which periodic discrete signal comprises a sampling of the measurements, (ii) based on the periodic discrete signal, computing a Hilbert transform and an analytic signal, the Hilbert transform being the imaginary component of the analytic signal, (iii) based on the analytic signal, computing instantaneous phase of the analytic signal, (iv) based on the instantaneous phase, outputting instructions; and (c) one or more transducers for outputting, based on the instructions, a signal that is phase-coordinated with the physiological signal and that affects the activity of neural tissue; wherein (1) the Hilbert transform has a point, t_now, that corresponds in time to the end of the periodic discrete signal, (2) the Hilbert transform ends later than t_now, at a distance from t_now that is equal to at least three-quarters of the period of the periodic discrete signal, and (3) the calculations include end-padding the periodic discrete signal to produce a padded signal and then smoothing the padded signal with a causal filter that introduces ringing artifacts into the padded signal. In some cases, the physiological signal is an electrical signal. In some cases, the physiological signal is motion caused by a physiological tremor. In some cases, the signal that affects the physiological signal is phase-coordinated with the physiological signal. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. An apparatus comprising:
   (a) one or more sensors that are configured to measure a physiological signal;
   (b) one or more computers that are programmed
      (i) to calculate a discrete signal that consists of samples of the physiological signal,
      (ii) to calculate a second signal, which second signal is a discrete Fourier transform of the discrete signal,
      (iii) to calculate a smoothed signal, by performing calculations that include (A) applying a causal filter to the second signal, which causal filter deforms a front-segment but not an end-segment of the second signal in such a way that the start point of the smoothed signal is equal in value to the endpoint of the smoothed signal, and (B) removing negative frequency components,
      (iv) to calculate an analytic signal, which analytic signal is equal to an inverse discrete Fourier transform of the smoothed signal,
      (v) to calculate, based on the analytic signal, instantaneous phase of the physiological signal, and
      (vi) to output instructions, based on the instantaneous phase; and
   (c) one or more transducers that are configured to output, based on the instructions, a neuromodulation signal.
2. The apparatus of claim 1, wherein the physiological signal is an electrical signal produced by neural tissue.
3. The apparatus of claim 1, wherein the physiological signal is motion caused by a muscular tremor.
4. The apparatus of claim 1, wherein phase of the neuromodulation signal is a function of phase of the physiological signal.
5. The apparatus of claim 1, wherein the neuromodulation signal comprises light.
6. The apparatus of claim 1, wherein the neuromodulation signal comprises sound.
7. The apparatus of claim 1, wherein the neuromodulation signal comprises electrical stimulation.
8. The apparatus of claim 1, wherein the one or more computers are programmed to calculate the smoothed signal based on:
   (a) a discrete Fourier transform of an impulse response of the causal filter;
   (b) a scrubber signal; and
   (c) the second signal.
9. The apparatus of claim 1, wherein:
   (a) the analytic signal has an imaginary component, which imaginary component is a Hilbert transform signal; and
   (b) the start point of the Hilbert transform signal is equal in value to the endpoint of the Hilbert transform signal.
10. An apparatus comprising:
    (a) one or more sensors that are configured to measure a physiological signal;
    (b) one or more computers that are programmed
       (i) to calculate a discrete signal that consists of samples of the physiological signal,
       (ii) to calculate a padded signal by front-padding, which front-padding adds a segment at the beginning of the discrete signal, which segment is a replica of an end-segment of the discrete signal,
       (iii) to calculate a modified signal, by performing calculations that comprise applying a causal filter to the padded signal and then removing data values that correspond in time to the segment added by the front-padding, which calculations cause the start point of the modified signal to have a value that (A) is different than the value of the start point of the padded signal and (B) is equal to the value of the endpoint of the modified signal,
       (iv) to calculate a fourth signal, which fourth signal is a discrete Fourier transform of the modified signal,
       (v) to calculate a fifth signal by removing negative frequency components from the fourth signal,
       (vi) to calculate an analytic signal, which analytic signal is equal to an inverse discrete Fourier transform of the fifth signal,
       (vii) to calculate, based on the analytic signal, instantaneous phase of the physiological signal, and
       (viii) to output instructions, based on the instantaneous phase; and
    (c) one or more transducers that are configured to output, based on the instructions, a neuromodulation signal.
11. The apparatus of claim 10, wherein phase of the neuromodulation signal is a function of phase of the physiological signal.
12. The apparatus of claim 10, wherein the one or more computers are further programmed to apply the causal filter to the padded signal by convolving (a) an impulse response of the causal filter and (b) the padded signal.
13. The apparatus of claim 10, wherein the neuromodulation signal comprises light, sound or electrical stimulation.
14. The apparatus of claim 10, wherein:
    (a) the analytic signal has an imaginary component, which imaginary component is a Hilbert transform signal; and
    (b) the start point of the Hilbert transform signal is equal in value to the endpoint of the Hilbert transform signal.

15. An apparatus comprising:
(a) one or more sensors that are configured to measure a physiological signal;
(b) one or more computers that are programmed
   (i) to calculate a discrete signal that consists of samples of the physiological signal,
   (ii) to create a padded signal by end-padding,
   (iii) to calculate a filtered signal, by applying a causal filter to the padded signal in such a way that the causal filter produces ringing artifacts which modify data values added by the end-padding,
   (iv) to calculate a fourth signal, which fourth signal is a discrete Fourier transform of the filtered signal,
   (v) to calculate a fifth signal by removing negative frequency components from the fourth signal,
   (vi) to calculate an analytic signal, which analytic signal is equal to an inverse discrete Fourier transform of the fifth signal,
   (vii) to calculate, based on the analytic signal, instantaneous phase of the physiological signal, and
   (viii) to output instructions, based on the instantaneous phase; and
(c) one or more transducers that are configured to output, based on the instructions, a neuromodulation signal.

16. The apparatus of claim 15, wherein the neuromodulation signal comprises light, sound or electrical stimulation.

17. The apparatus of claim 15, wherein phase of the neuromodulation signal is a function of phase of the physiological signal.

18. The apparatus of claim 15, wherein the one or more computers are further programmed to apply the causal filter to the padded signal by convolving (a) an impulse response of the causal filter and (b) the padded signal.

19. The apparatus of claim 15, wherein the one or more computers are further programmed to truncate the padded signal by removing a front-segment of the padded signal, before applying the causal filter.

20. The apparatus of claim 15, wherein:
(a) the physiological signal is a periodic signal; and
(b) the end-padding comprises adding a segment that consists of data values and is at least as long as three quarters of a period of the discrete signal.

\* \* \* \* \*